US010441644B2

(12) United States Patent
Okada et al.

(10) Patent No.: US 10,441,644 B2
(45) Date of Patent: Oct. 15, 2019

(54) H3.3 CTL PEPTIDES AND USES THEREOF

(71) Applicant: Regents of the University of California, Oakland, CA (US)

(72) Inventors: Hideho Okada, Mill Valley, CA (US); Yafei Hou, Palo Alto, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 15/613,837

(22) Filed: Jun. 5, 2017

(65) Prior Publication Data

US 2017/0281742 A1    Oct. 5, 2017

Related U.S. Application Data

(63) Continuation-in-part of application No. PCT/US2016/030849, filed on May 4, 2016.

(60) Provisional application No. 62/157,362, filed on May 5, 2015, provisional application No. 62/212,508, filed on Aug. 31, 2015.

(51) Int. Cl.
*A61K 38/03* (2006.01)
*A61K 38/17* (2006.01)
*A61K 38/19* (2006.01)
*C07K 14/47* (2006.01)
*A61K 39/00* (2006.01)
*G01N 33/50* (2006.01)

(52) U.S. Cl.
CPC .......... *A61K 39/0011* (2013.01); *A61K 38/03* (2013.01); *A61K 38/17* (2013.01); *A61K 38/1764* (2013.01); *A61K 38/19* (2013.01); *C07K 14/4748* (2013.01); *G01N 33/505* (2013.01); *G01N 33/5014* (2013.01)

(58) Field of Classification Search
CPC ............ A61K 2309/5158; A61K 38/03; A61K 38/17; A61K 38/1764; A61K 38/19; A61K 39/0011; C07K 14/47; C07K 14/4748; C12N 5/0638; G01N 33/5014; G01N 33/505
USPC ............. 530/300, 327, 328, 388.75; 514/1.1, 514/21.5, 21.6
See application file for complete search history.

(56) References Cited

U.S. PATENT DOCUMENTS

| | | |
|---|---|---|
| 4,179,337 A | 12/1979 | Davis et al. |
| 4,235,871 A | 11/1980 | Papahadjopoulos et al. |
| 4,495,285 A | 1/1985 | Shimizu et al. |
| 4,501,728 A | 2/1985 | Geho et al. |
| 4,609,546 A | 9/1986 | Hiratani |
| 4,766,106 A | 8/1988 | Katre et al. |
| 4,837,028 A | 6/1989 | Allen |
| 5,019,369 A | 5/1991 | Presant et al. |
| 5,464,758 A | 11/1995 | Gossen et al. |
| 5,589,362 A | 12/1996 | Bujard et al. |
| 5,650,298 A | 7/1997 | Bujard et al. |
| 5,656,465 A | 8/1997 | Panicali et al. |
| 5,736,142 A | 4/1998 | Sette et al. |
| 5,830,462 A | 11/1998 | Crabtree et al. |
| 5,833,975 A | 11/1998 | Paoletti et al. |
| 5,869,337 A | 2/1999 | Crabtree et al. |
| 5,876,735 A | 3/1999 | Reed |
| 6,218,371 B1 | 4/2001 | Krieg et al. |
| 8,652,462 B2 | 2/2014 | Leguern |
| 9,388,213 B2 | 7/2016 | Allis et al. |
| 2007/0044171 A1 | 2/2007 | Kovalic et al. |
| 2013/0236906 A1 | 9/2013 | Dobosz et al. |
| 2013/0259891 A1 | 10/2013 | Harn et al. |
| 2014/0107039 A1 | 4/2014 | Allis et al. |
| 2016/0120905 A1 | 5/2016 | Galetto et al. |
| 2016/0145352 A1 | 5/2016 | Mirey et al. |
| 2017/0067021 A1 | 3/2017 | Moriarity et al. |
| 2018/0155403 A1* | 6/2018 | Platten .............. C07K 14/4748 |

FOREIGN PATENT DOCUMENTS

| | | |
|---|---|---|
| EP | 0 268 110 A1 | 5/1988 |
| EP | 0 268 110 B1 | 5/1988 |
| EP | 0 270 799 A1 | 6/1988 |
| EP | 0 270 799 B1 | 6/1988 |
| EP | 2 172 547 A1 | 4/2010 |
| EP | 2 172 547 B2 | 4/2010 |
| WO | WO-94/18317 A1 | 8/1994 |
| WO | WO-95/07707 A1 | 3/1995 |
| WO | WO-96/06111 A1 | 2/1996 |
| WO | WO-96/41865 A1 | 12/1996 |
| WO | WO-00/001822 A1 | 1/2000 |
| WO | WO-01/72784 A2 | 10/2001 |
| WO | WO-01/72784 A3 | 10/2001 |
| WO | WO-02/18418 A1 | 3/2002 |
| WO | WO-03/098223 A2 | 11/2003 |
| WO | WO-03/098223 A3 | 11/2003 |
| WO | WO-2004/080288 A2 | 9/2004 |
| WO | WO-2004/080288 A3 | 9/2004 |
| WO | WO-2005/000332 A2 | 1/2005 |
| WO | WO-2005/000332 A3 | 1/2005 |

(Continued)

OTHER PUBLICATIONS

Cuthbert et al., Histone Deimination Antagonizes Arginine Methylation, Cell, vol. 118. Sep. 3, 2004, 545-553.
International Search Report in PCT/US2016/030849, dated Aug. 18, 2016.
Al-Lazikani, B. et al. (Nov. 7, 1997). "Standard conformations for the canonical structures of immunoglobulins," *J Mol Biol* 273(4):927-948.
Bassani-Sternberg, M. et al. (Mar. 2015, e-published Jan. 9, 2015). "Mass spectrometry of human leukocyte antigen class I peptidomes reveals strong effects of protein abundance and turnover on antigen presentation," Mol Cell Proteomics 14(3):658-673.
Batzer, M.A. et al. (Sep. 25, 1991, e-published Jan. 9, 2015). "Enhanced evolutionary PCR using oligonucleotides with inosine at the 3'-terminus," *Nucleic Acids Res* 19(18):5081.

(Continued)

*Primary Examiner* — Julie Ha
(74) *Attorney, Agent, or Firm* — Mintz Levin Cohn Ferris Glovsky and Popeo PC

(57) ABSTRACT

Peptides that generate an immune response to glioma-related H3.3 proteins and methods of their use are provided.

4 Claims, 17 Drawing Sheets

Specification includes a Sequence Listing.

(56) References Cited

FOREIGN PATENT DOCUMENTS

| WO | WO-2005/028620 A2 | 3/2005 |
|---|---|---|
| WO | WO-2005/028620 A3 | 3/2005 |
| WO | WO-2005/124337 A2 | 12/2005 |
| WO | WO-2005/124337 A3 | 12/2005 |
| WO | WO-2006/057009 A1 | 6/2006 |
| WO | WO-2008/153029 A1 | 12/2008 |
| WO | WO-2009/147201 A2 | 12/2009 |
| WO | WO-2009/147201 A3 | 12/2009 |
| WO | WO-2010/033658 A2 | 3/2010 |
| WO | WO-2010/033658 A3 | 3/2010 |
| WO | WO-2010/117694 A2 | 10/2010 |
| WO | WO-2010/117694 A3 | 10/2010 |
| WO | WO-2010/120942 A2 | 10/2010 |
| WO | WO-2010/120942 A3 | 10/2010 |
| WO | WO-2011/008850 A2 | 1/2011 |
| WO | WO-2011/008850 A9 | 1/2011 |
| WO | WO-2011/070172 A1 | 6/2011 |
| WO | WO-2012/001103 A1 | 1/2012 |
| WO | WO-2012/038055 A1 | 3/2012 |
| WO | WO-2012/123119 A1 | 9/2012 |
| WO | WO-2013/075237 A1 | 5/2013 |
| WO | WO-2014/083173 A1 | 6/2014 |
| WO | WO-2014/124227 A1 | 8/2014 |
| WO | WO-2014/127200 A1 | 8/2014 |
| WO | WO-2014/190035 A2 | 11/2014 |
| WO | WO-2014/190035 A3 | 12/2014 |
| WO | WO-2014/202745 A1 | 12/2014 |
| WO | WO-2014/210545 A2 | 12/2014 |
| WO | WO-2014/210545 A3 | 12/2014 |
| WO | WO-2015/200260 A1 | 12/2015 |
| WO | WO-2016/057398 A1 | 4/2016 |
| WO | WO-2016/164392 A1 | 10/2016 |
| WO | WO-2017/009349 A1 | 1/2017 |

OTHER PUBLICATIONS

Beaucage (1981). "Deoxynucleoside Phosphoramidites—A New Class of Key Intermediates for Deoxypolynucleotide Synthesis," *Tetra.Letts.* 22:1859-1862.

Cheng, Y. et al. (Dec. 1, 1973). "Relationship between the inhibition constant (K1) and the concentration of inhibitor which causes 50 per cent inhibition ($I_{50}$) of an enzymatic reaction," *Biochem Pharmacol* 22(23):3099-3108.

Chothia, C. et al. (Aug. 20, 1987). "Canonical structures for the hypervariable regions of immunoglobulins," *J Mol Biol* 196(4):901-917.

Chothia, C. et al. (Dec. 21-28, 1989). "Conformations of immunoglobulin hypervariable regions," *Nature* 342(6252):877-883.

Chothia, C. et al. (Oct. 5, 1992). "Structural repertoire of the human VH segments," *J Mol Biol* 227(3):799-817.

Coos Verhoef, J. et al. (Oct.-Dec. 1986). "Des-enkephalin-γ-endorphin (DEγE): biotransformation in rat, dog and human plasma," *Eur J Drug Metab Pharmacokinet* 11(4):291-302.

Database Accession No. AZU40581 (May 10, 2012). "Providing antigen-specific lymphoid cells comprises introducing a nucleic acid encoding a T cell receptor into a lymphoid cell," 2 pages.

Extended European Search Report dated Nov. 22, 2018, for EP Application No. 16790043.0, 14 pages.

Fukazawa, T. et al. (Feb. 1994). "Testing the importance of each residue in a HLA-B27-binding peptide using monoclonal antibodies," *J Immunol* 152(3):1190-1196.

Gossen, M. et al. (Jun. 15, 1992). "Tight control of gene expression in mammalian cells by tetracycline-responsive promoters," PNAS USA 89(12):5547-5551.

Gulukota, K. et al. (Apr. 18, 1997). "Two complementary methods for predicting peptides binding major histocompatibility complex molecules," *J Mol Biol* 267(5):1258-1267.

Heemskerk, M.H. et al. (Nov. 15, 2003, e-published Jul. 17, 2003). "Redirection of antileukemic reactivity of peripheral T lymphocytes using gene transfer of minor histocompatibility antigen HA-2-specific T-cell receptor complexes expressing a conserved alpha joining region," *Blood* 102(10):3530-3540.

Huston, J.S. et al. (Aug. 1988). "Protein engineering of antibody binding sites: recovery of specific activity in an anti-digoxin single-chain Fv analogue produced in *Escherichia coli*," *PNAS USA* 85(16):5879-5883.

Hou, Y. et al. (Nov. 4, 2015). "Novel and shared neoantigen for glioma T cell therapy derived from histone 3 variant H3.3 K27M mutation," *Journal for Immunotherapy of Cancer* 3(Suppl 2):P445, 2 pages.

Kovalic D.K. et al. (Feb. 22, 2017). "New recombinant polynucleotide, useful in improving plant cold, heat, drought or herbicide tolerance or tolerance to extreme osmotic conditions, or to pathogens or pests, or in manipulating growth rate in plant cells," SEQ ID No 152042, Database Accession No. AOI09238, 2 pages.

LeFranc, M.P. (Jan. 1, 2001). "IMGT, the international ImMunoGeneTics database," *Nucleic Acids Res* 29(1):207-209.

Lewis, P.W. et al. (May 17, 2013, e-published Mar. 28, 2013). "Inhibition of PRC2 activity by a gain-of-function H3 mutation found in pediatric glioblastoma," *Science* 340(6134):857-861.

Maccallum, R.M. et al. (Oct. 11, 1996). "Antibody-antigen interactions: contact analysis and binding site topography," *J Mol Biol* 262(5):732-745.

Martin, A.C. et al. (Dec. 1989). "Modeling antibody hypervariable loops: a combined algorithm," *PNAS USA* 86(23):9268-9272.

Martin, A.C. et al. (1991). "Molecular modeling of antibody combining sites," *Methods Enzymol* 203:121-153.

Matteucci M.D. et al. (1981). "Synthesis of deoxyoligonucleotides on a polymer support," *J Am Chem Soc* 103(11):3185-3191.

Ohno, M. et al. (Dec. 16, 2013). "Expression of miR-17-92 enhances anti-tumor activity of T-cells transduced with the anti-EGFRvIII chimeric antigen receptor in mice bearing human GBM xenografts," *J Immunother Cancer* 1:21.

Ohtsuka, E. et al. (Mar. 1985). "An alternative approach to deoxyoligonucleotides as hybridization probes by insertion of deoxyinosine at ambiguous codon positions," *J Biol Chem* 260(5):2605-2608.

Okamoto, S. et al. (Dec. 1, 2009, e-published Nov. 10, 2009). "Improved expression and reactivity of transduced tumor-specific TCRs in human lymphocytes by specific silencing of endogenous TCR," *Cancer Res* 69(23):9003-9011.

Okamoto, S. et al. (Dec. 18, 2012). "A Promising Vector for TCR Gene Therapy: Differential Effect of siRNA, 2A Peptide, and Disulfide Bond on the Introduced TCR Expression," *Mol Ther Nucleic Acids* 1:e63.

Pedersen, J. et al. (Oct. 1992). "Antibody modeling: Beyond homology," *Immunomethods* 1(2):126-136.

Rees, A.R. et al. (1996). "Antibody combining sites: structure and prediction," in *A Protein Structure Prediction* Sternberg M.J.E. (ed.), Oxford University Press, Oxford, 141-172.

Rossolini, G.M. et al. (Apr. 1994). "Use of deoxyinosine-containing primers vs degenerate primers for polymerase chain reaction based on ambiguous sequence information," *Mol Cell Probes* 8(2):91-98.

Ruiz, M. et al. (Jan. 1, 2000). "IMGT, the international ImMunoGeneTics database," *Nucleic Acids Res* 28(1):219-221.

Sidney, J. et al. (Feb. 2013). "Measurement of MHC/peptide interactions by gel filtration or monoclonal antibody capture," *Curr Protoc Immunol* Chapter 18:Unit18.3.

Vanan, M.I. et al. (Dec. 2014, e-published Sep. 12, 2014). "Management of high-grade gliomas in the pediatric patient: Past, present, and future," *Neurooncol Pract* 1(4):145-157.

Wooldridge, L. et al. (Feb. 2009). "Tricks with tetramers: how to get the most from multimeric peptide-MHC," *Immunology* 126(2):147-164.

Written Opinion dated Aug. 18, 2016, for PCT Application No. PCT/US2016/030849, filed May 4, 2016.

Yokouchi, H. et al. (Feb. 2006). "Tetramer-blocking assay for defining antigen-specific cytotoxic T lymphocytes using peptide-MHC tetramer," *Cancer Sci* 97(2):148-154.

\* cited by examiner

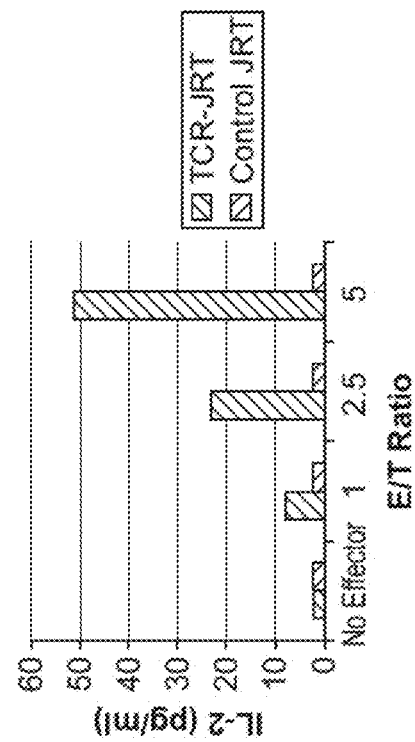
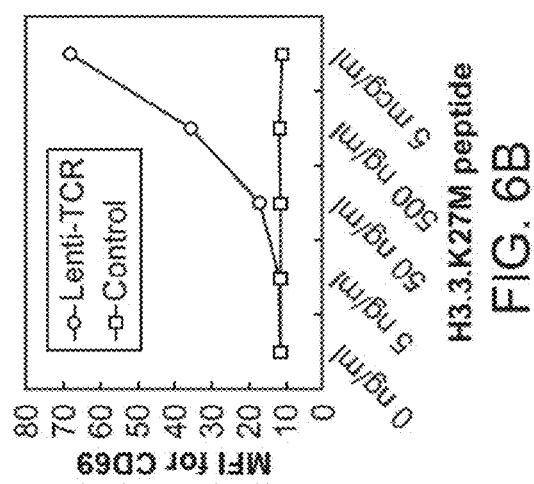
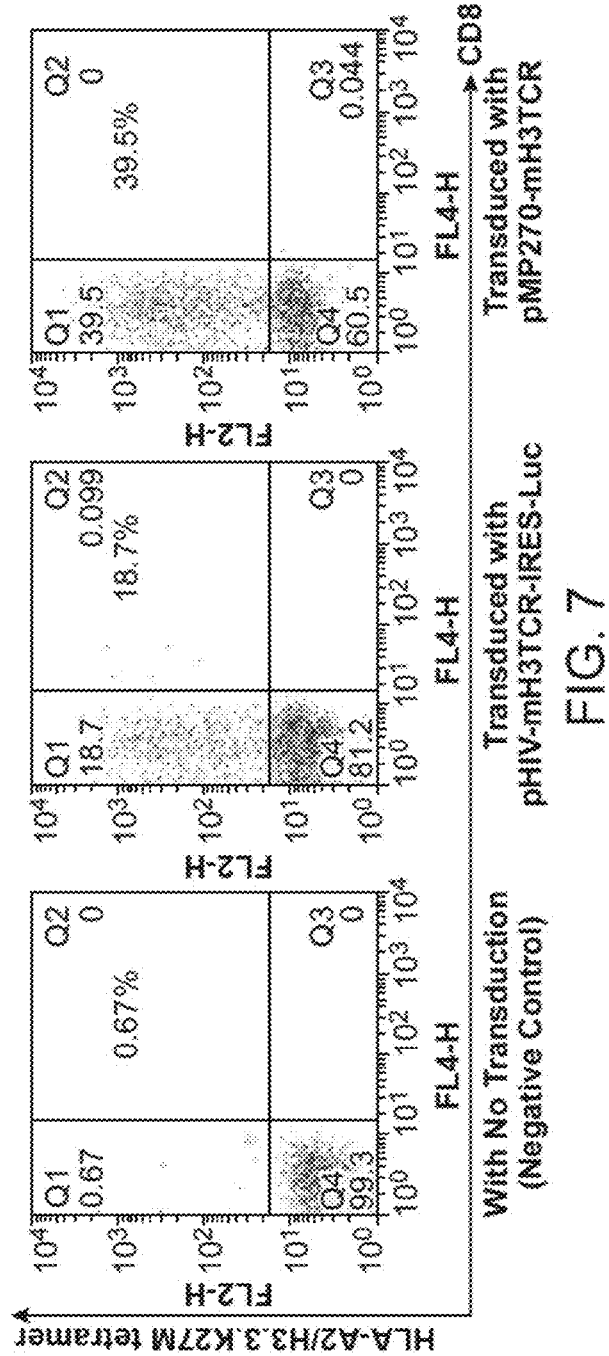
FIG. 6B
FIG. 6C
FIG. 7

SEQUENCE LISTING

<160> NUMBER OF SEQ ID NOS: 22

<210> SEQ ID NO 1
<211> LENGTH: 10
<212> TYPE: PRT
<213> ORGANISM: Artificial Sequence
<220> FEATURE:
<223> OTHER INFORMATION: synthetic peptide construct
<220> FEATURE:
<221> NAME/KEY: MOD_RES
<222> LOCATION: (1)..(1)
<223> OTHER INFORMATION: Xaa is Arg or Ala
<220> FEATURE:
<221> NAME/KEY: MOD_RES
<222> LOCATION: (1)..(1)
<223> OTHER INFORMATION: Xaa is Arg or Ala; when Xaa is Arg,
      citrullination of Arg may be present or absent
<220> FEATURE:
<221> NAME/KEY: MOD_RES
<222> LOCATION: (6)..(6)
<223> OTHER INFORMATION: Xaa is Ser or Ala

<400> SEQUENCE: 1

Xaa Met Ser Ala Pro Xaa Thr Gly Gly Val
1               5                   10

<210> SEQ ID NO 2
<211> LENGTH: 10
<212> TYPE: PRT
<213> ORGANISM: Artificial Sequence
<220> FEATURE:
<223> OTHER INFORMATION: synthetic peptide construct

<400> SEQUENCE: 2

Arg Met Ser Ala Pro Ser Thr Gly Gly Val
1               5                   10

<210> SEQ ID NO 3
<211> LENGTH: 10
<212> TYPE: PRT
<213> ORGANISM: Artificial Sequence
<220> FEATURE:
<223> OTHER INFORMATION: synthetic peptide construct

<400> SEQUENCE: 3

Arg Lys Ser Ala Pro Ser Thr Gly Gly Val
1               5                   10

<210> SEQ ID NO 4

<400> SEQUENCE: 4

000

<210> SEQ ID NO 5
<211> LENGTH: 10
<212> TYPE: PRT
<213> ORGANISM: Artificial Sequence
<220> FEATURE:
<223> OTHER INFORMATION: synthetic peptide construct

<400> SEQUENCE: 5

Ala Met Ser Ala Pro Ser Thr Gly Gly Val
1               5                   10

<210> SEQ ID NO 6
<211> LENGTH: 10
<212> TYPE: PRT
<213> ORGANISM: Artificial Sequence

```
<220> FEATURE:
<223> OTHER INFORMATION: synthetic peptide construct

<400> SEQUENCE: 6

Arg Met Ser Ala Pro Ala Thr Gly Gly Val
1               5                   10

<210> SEQ ID NO 7
<211> LENGTH: 10
<212> TYPE: PRT
<213> ORGANISM: Artificial Sequence
<220> FEATURE:
<223> OTHER INFORMATION: synthetic peptide construct

<400> SEQUENCE: 7

Ala Met Ser Ala Pro Ala Thr Gly Gly Val
1               5                   10

<210> SEQ ID NO 8
<211> LENGTH: 273
<212> TYPE: PRT
<213> ORGANISM: Artificial Sequence
<220> FEATURE:
<223> OTHER INFORMATION: synthetic peptide construct

<400> SEQUENCE: 8

Met Leu Thr Ala Ser Leu Leu Arg Ala Val Ile Ala Ser Ile Cys Val
1               5                   10                  15

Val Ser Ser Met Ala Gln Lys Val Thr Gln Ala Gln Thr Glu Ile Ser
            20                  25                  30

Val Val Glu Lys Glu Asp Val Thr Leu Asp Cys Val Tyr Glu Thr Arg
        35                  40                  45

Asp Thr Thr Tyr Tyr Leu Phe Trp Tyr Lys Gln Pro Pro Ser Gly Glu
    50                  55                  60

Leu Val Phe Leu Ile Arg Arg Asn Ser Phe Asp Glu Gln Asn Glu Ile
65                  70                  75                  80

Ser Gly Arg Tyr Ser Trp Asn Phe Gln Lys Ser Thr Ser Ser Phe Asn
                85                  90                  95

Phe Thr Ile Thr Ala Ser Gln Val Val Asp Ser Ala Val Tyr Phe Cys
            100                 105                 110

Ala Leu Ser Glu Glu Asn Asp Met Arg Phe Gly Ala Gly Thr Arg Leu
        115                 120                 125

Thr Val Lys Pro Asn Ile Gln Asn Pro Asp Pro Ala Val Tyr Gln Leu
    130                 135                 140

Arg Asp Ser Lys Ser Ser Asp Lys Ser Val Cys Leu Phe Thr Asp Phe
145                 150                 155                 160

Asp Ser Gln Thr Asn Val Ser Gln Ser Lys Asp Ser Asp Val Tyr Ile
                165                 170                 175

Thr Asp Lys Thr Val Leu Asp Met Arg Ser Met Asp Phe Lys Ser Asn
            180                 185                 190

Ser Ala Val Ala Trp Ser Asn Lys Ser Asp Phe Ala Cys Ala Asn Ala
        195                 200                 205

Phe Asn Asn Ser Ile Ile Pro Glu Asp Thr Phe Phe Pro Ser Pro Glu
    210                 215                 220

Ser Ser Cys Asp Val Lys Leu Val Glu Lys Ser Phe Glu Thr Asp Thr
225                 230                 235                 240

Asn Leu Asn Phe Gln Asn Leu Ser Val Ile Gly Phe Arg Ile Leu Leu
                245                 250                 255
```

```
Leu Lys Val Ala Gly Phe Asn Leu Leu Met Thr Leu Arg Leu Trp Ser
            260                 265                 270

Ser
```

<210> SEQ ID NO 9
<211> LENGTH: 822
<212> TYPE: DNA
<213> ORGANISM: Artificial Sequence
<220> FEATURE:
<223> OTHER INFORMATION: synthetic nucleotide sequence

<400> SEQUENCE: 9

```
atgctgactg ccagcctgtt gagggcagtc atagcctcca tctgtgttgt atccagcatg      60
gctcagaagg taactcaagc gcagactgaa atttctgtgg tggagaagga ggatgtgacc     120
ttggactgtg tgtatgaaac ccgtgatact acttattact tattctgtta caagcaacca     180
ccaagtggag aattggtttt ccttattcgt cggaactctt ttgatgagca aatgaaata     240
agtggtcggt attcttggaa cttccagaaa tccaccagtt ccttcaactt caccatcaca     300
gcctcacaag tcgtggactc agcagtatac ttctgtgctc tgagtgagga aatgacatg      360
cgctttggag cagggaccag actgacagta aaaccaaata tccagaaccc tgaccctgcc     420
gtgtaccagc tgagagactc taaatccagt gacaagtctg tctgcctatt caccgatttt     480
gattctcaaa caaatgtgtc acaaagtaag gattctgatg tgtatatcac agacaaaact     540
gtgctagaca tgaggtctat ggacttcaag agcaacagtg ctgtggcctg gagcaacaaa     600
tctgactttg catgtgcaaa cgccttcaac aacagcatta ttccagaaga caccttcttc     660
cccagcccag aaagttcctg tgatgtcaag ctggtcgaga aaagctttga acagatacg      720
aacctaaact ttcaaaaacct gtcagtgatt gggttccgaa tcctcctcct gaaagtggcc     780
gggtttaatc tgctcatgac gctgcggctg tggtccagct ga                       822
```

<210> SEQ ID NO 10
<211> LENGTH: 311
<212> TYPE: PRT
<213> ORGANISM: Artificial Sequence
<220> FEATURE:
<223> OTHER INFORMATION: synthetic peptide construct

<400> SEQUENCE: 10

```
Met Gly Pro Gln Leu Leu Gly Tyr Val Val Leu Cys Leu Leu Gly Ala
1               5                   10                  15

Gly Pro Leu Glu Ala Gln Val Thr Gln Asn Pro Arg Tyr Leu Ile Thr
            20                  25                  30

Val Thr Gly Lys Lys Leu Thr Val Thr Cys Ser Gln Asn Met Asn His
        35                  40                  45

Glu Tyr Met Ser Trp Tyr Arg Gln Asp Pro Gly Leu Gly Leu Arg Gln
    50                  55                  60

Ile Tyr Tyr Ser Met Asn Val Glu Val Thr Asp Lys Gly Asp Val Pro
65                  70                  75                  80

Glu Gly Tyr Lys Val Ser Arg Lys Glu Lys Arg Asn Phe Pro Leu Ile
                85                  90                  95

Leu Glu Ser Pro Asn Pro Asn Gln Thr Ser Leu Tyr Phe Cys Ala Ser
            100                 105                 110

Gly Trp Gly Gly Pro Phe Tyr Glu Gln Tyr Phe Gly Pro Gly Thr Arg
        115                 120                 125

Leu Thr Val Thr Glu Asp Leu Lys Asn Val Phe Pro Pro Glu Val Ala
    130                 135                 140
```

Val Phe Glu Pro Ser Glu Ala Glu Ile Ser His Thr Gln Lys Ala Thr
145                 150                 155                 160

Leu Val Cys Leu Ala Thr Gly Phe Tyr Pro Asp His Val Glu Leu Ser
                165                 170                 175

Trp Trp Val Asn Gly Lys Glu Val His Ser Gly Val Ser Thr Asp Pro
            180                 185                 190

Gln Pro Leu Lys Glu Gln Pro Ala Leu Asn Asp Ser Arg Tyr Cys Leu
        195                 200                 205

Ser Ser Arg Leu Arg Val Ser Ala Thr Phe Trp Gln Asn Pro Arg Asn
    210                 215                 220

His Phe Arg Cys Gln Val Gln Phe Tyr Gly Leu Ser Glu Asn Asp Glu
225                 230                 235                 240

Trp Thr Gln Asp Arg Ala Lys Pro Val Thr Gln Ile Val Ser Ala Glu
                245                 250                 255

Ala Trp Gly Arg Ala Asp Cys Gly Phe Thr Ser Glu Ser Tyr Gln Gln
                260                 265                 270

Gly Val Leu Ser Ala Thr Ile Leu Tyr Glu Ile Leu Leu Gly Lys Ala
            275                 280                 285

Thr Leu Tyr Ala Val Leu Val Ser Ala Leu Val Leu Met Ala Met Val
        290                 295                 300

Lys Arg Lys Asp Ser Arg Gly
305                 310

<210> SEQ ID NO 11
<211> LENGTH: 936
<212> TYPE: DNA
<213> ORGANISM: Artificial Sequence
<220> FEATURE:
<223> OTHER INFORMATION: synthetic nucleotide sequence

<400> SEQUENCE: 11 atgggcccc agctccttgg ctatgtggtc ctttgccttc taggagcagg ccccctggaa      60
gcccaagtga cccagaaccc aagataccct catcacagtga ctggaaagaa gttaacagtg    120
acttgttctc agaatatgaa ccatgagtat atgtcctggt atcgacaaga cccagggctg    180
ggcttaaggc agatctacta ttcaatgaat gttgaggtga ctgataaggg agatgttcct    240
gaagggtaca agtctctcg aaaagagaag aggaatttcc ccctgatcct ggagtcgccc     300
aaccccaacc agacctctct gtacttctgt gccagcggct ggggtggtcc attctacgag    360
cagtacttcg gccgggcac caggctcacg gtcacagagg acctgaaaaa cgtgttccca    420
cccgaggtcg ctgtgtttga gccatcagaa gcagagatct cccacaccca aaaggccaca    480
ctggtatgcc tggccacagg cttctacccc gaccacgtgg agctgagctg gtgggtgaat    540
gggaaggagg tgcacagtgg ggtcagcaca gacccgcagc ccctcaagga gcagcccgcc    600
ctcaatgact ccagatactg cctgagcagc cgcctgaggg tctcggccac cttctggcag    660 aaccccgca accacttccg ctgtcaagtc cagttctacg gctctcggga gaatgacgag    720
tggacccagg atagggccaa acccgtcacc cagatcgtca gcgccgaggc ctggggtaga    780
gcagactgtg gcttcacctc cgagtcttac cagcaagggg tcctgtctgc caccatcctc    840
tatgagatct gctagggaa ggccaccttg tatgccgtgc tggtcagtgc cctcgtgctg    900
atggccatgg tcaagagaaa ggattccaga ggctag                              936

<210> SEQ ID NO 12
<211> LENGTH: 7

```
<212> TYPE: PRT
<213> ORGANISM: Artificial Sequence
<220> FEATURE:
<223> OTHER INFORMATION: synthetic peptide construct

<400> SEQUENCE: 12

Thr Arg Asp Thr Thr Tyr Tyr
1               5

<210> SEQ ID NO 13
<211> LENGTH: 4
<212> TYPE: PRT
<213> ORGANISM: Artificial Sequence
<220> FEATURE:
<223> OTHER INFORMATION: synthetic peptide construct

<400> SEQUENCE: 13

Arg Asn Ser Phe
1

<210> SEQ ID NO 14
<211> LENGTH: 4
<212> TYPE: PRT
<213> ORGANISM: Artificial Sequence
<220> FEATURE:
<223> OTHER INFORMATION: synthetic peptide construct

<400> SEQUENCE: 14

Ala Leu Ser Glu
1

<210> SEQ ID NO 15
<211> LENGTH: 6
<212> TYPE: PRT
<213> ORGANISM: Artificial Sequence
<220> FEATURE:
<223> OTHER INFORMATION: synthetic peptide construct

<400> SEQUENCE: 15

Asn Met Asn His Glu Tyr
1               5

<210> SEQ ID NO 16
<211> LENGTH: 8
<212> TYPE: PRT
<213> ORGANISM: Artificial Sequence
<220> FEATURE:
<223> OTHER INFORMATION: synthetic peptide construct

<400> SEQUENCE: 16

Tyr Ser Met Asn Val Glu Val Thr
1               5

<210> SEQ ID NO 17
<211> LENGTH: 13
<212> TYPE: PRT
<213> ORGANISM: Artificial Sequence
<220> FEATURE:
<223> OTHER INFORMATION: synthetic peptide construct

<400> SEQUENCE: 17

Cys Ala Ser Gly Trp Gly Gly Pro Phe Tyr Glu Gln Tyr
1               5                   10

<210> SEQ ID NO 18
<211> LENGTH: 10
<212> TYPE: PRT
```

```
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Xaa is citrulline

<400> SEQUENCE: 18

Xaa Met Ser Ala Pro Ser Thr Gly Gly Val
1               5                   10

<210> SEQ ID NO 19
<211> LENGTH: 9
<212> TYPE: PRT
<213> ORGANISM: Artificial Sequence
<220> FEATURE:
<223> OTHER INFORMATION: Synthetic peptide

<400> SEQUENCE: 19

Gly Ile Leu Gly Phe Val Phe Thr Leu
1               5

<210> SEQ ID NO 20
<211> LENGTH: 10
<212> TYPE: PRT
<213> ORGANISM: Hepatitis B virus

<400> SEQUENCE: 20

Phe Leu Pro Ser Asp Tyr Phe Pro Ser Val
1               5                   10

<210> SEQ ID NO 21
<211> LENGTH: 18
<212> TYPE: DNA
<213> ORGANISM: Artificial Sequence
<220> FEATURE:
<223> OTHER INFORMATION: Synthetic primer

<400> SEQUENCE: 21
tgtaaaacga cggccagt                                                 18

<210> SEQ ID NO 22
<211> LENGTH: 17
<212> TYPE: DNA
<213> ORGANISM: Artificial Sequence
<220> FEATURE:
<223> OTHER INFORMATION: Synthetic primer

<400> SEQUENCE: 22
caggaaacag ctatgac                                                  17
```

H3.3 CTL PEPTIDES AND USES THEREOF

CROSS-REFERENCE TO RELATED PATENT APPLICATIONS

The present patent application is a continuation-in-part of PCT/US16/30849, filed May 4, 2016, which claims benefit of priority to U.S. Provisional Patent Application No. 62/157,362, filed May 5, 2015, and U.S. Provisional Patent Application No. 62/212,508, filed Aug. 31, 2015, each of which are incorporated by reference.

STATEMENT AS TO RIGHTS TO INVENTIONS MADE UNDER FEDERALLY SPONSORED RESEARCH AND DEVELOPMENT

This invention was made with government support under grant no. R21 NS083171 awarded by the National Institutes of Health. The government has certain rights in the invention.

REFERENCE TO A "SEQUENCE LISTING" SUBMITTED AS ASCII TEXT FILES VIA EFS-WEB

The Sequence Listing written in file 081906-220420US-1048132_SequenceListing.txt created on May 22, 2017, 11,863 bytes, machine format IBM-PC, MS-Windows operating system, in accordance with 37 C.F.R. §§ 1.821- to 1.825, is hereby incorporated by reference in its entirety for all purposes.

BACKGROUND OF THE INVENTION

Malignant gliomas, including glioblastomas (GBM), diffuse intrinsic pontine gliomas (DIPG), ependymomas, astrocytomas, oligodendrogliomas, brainstem glioma, thalamic gliomas, spinal cord gliomas, and optic nerve glioma, are lethal brain tumors in both adults and children. Recent genetic studies have revealed that malignant gliomas in children and young adults often show recurrent missense mutations in H3F3A, which encodes the replication-independent histone 3 variant H3.3. See, e.g., Lewis et al., *Science* Vol. 340 no. 6134 pp. 857-861 (2013). Approximately 30% of overall GBM and 70% of DIPG cases harbor the amino-acid substitution from lysine (K) to methionine (M) at the position 27 of H3.3 (K27M mutation, hereafter), which is universally associated with shorter survival in DIPG patients compared with patients with non-mutated H3.3. The adaptive immune system, such as T lymphocytes (T cells hereafter), are normally tolerant to normal self-proteins, but can recognize mutated amino-acids as non-self. Hence cancer-specific mutations can be suitable targets of cancer immunotherapy, such as cancer vaccines and adoptive T cell transfer therapy.

BRIEF SUMMARY OF THE INVENTION

In some embodiments, an isolated peptide consisting of less than 100, 75, 50, or 30 amino acids is provided, wherein the peptide comprises (R/A)MSAP(S/A)TGGV (SEQ ID NO:1 In some embodiments, the peptide consists of 10-14 amino acids. In some embodiments, the peptide consists of (R/A)MSAP(S/A)TGGV (SEQ ID NO:1). In some embodiments, the R in SEQ ID NO:1 is citrullinated. In some embodiments, the R in SEQ ID NO:1 is not citrullinated.

Also provided is a fluorochrome-conjugated peptide-major histocompatibility complex (pMHC) multimer, wherein the peptide is as described above or elsewhere herein.

Also provided is a nucleic acid, optionally isolated or purified, encoding the peptide as described above or elsewhere herein. In some embodiments, the nucleic acid is a plasmid or a viral vector. In some embodiments, the vector is capable of delivering the nucleic acid into an antigen presenting cell (APC).

Also provided is a cell comprising a heterologous peptide consisting of 10-12 or 10-14 (e.g., 10, 11, 12, 13, or 14) amino acids, wherein the peptide comprises (R/A)MSAP(S/A)TGGV (SEQ ID NO:1). In some embodiments, the peptide consists of (R/A)MSAP(S/A)TGGV (SEQ ID NO:1). In some embodiments, the R in SEQ ID NO:1 is citrullinated. In some embodiments, the R in SEQ ID NO:1 is not citrullinated. In some embodiments, the cell is an antigen presenting cell (APC). In some embodiments, the cell is a bacterial cell. In some embodiments, the bacterial cell is *E. coli* or *Listeria monocytogenes*. In some embodiments, the APC presents the heterologous peptide on the surface of the cell. In some embodiments, the APC comprises a heterologous expression cassette comprising a promoter operably linked to a polynucleotide encoding the peptide.

Also provided is a method of inducing an immune response in a human individual. In some embodiments, the method comprises administering a sufficient amount of the APC as described above or elsewhere herein to the human individual, thereby inducing an immune response in the human individual to replication-independent histone 3 variant H3.3 or H3.1. In some embodiments, the APC is from the individual (autologous). In some embodiments, the immune response is a cytotoxic T-cell response. In some embodiments, the human individual has a glioma. In some embodiments, the individual carries an HLA-*0201, HLA-*0202, HLA-*0203, HLA-*0204, HLA-*0205, HLA-*0206, HLA-*0207, or HLA-*0211 allele.

Also provided is a composition for stimulating an immune response to replication-independent histone 3 variant H3.3, the composition comprises a peptide consisting of 10-12 or 10-14 (e.g., 10, 11, 12, 13, or 14) amino acids, wherein the peptide comprises (R/A)MSAP(S/A)TGGV (SEQ ID NO:1). In some embodiments, the composition comprises a peptide consisting of (R/A)MSAP(S/A)TGGV (SEQ ID NO:1). In some embodiments, the composition further comprises an adjuvant. In some embodiments, the R in SEQ ID NO:1 is citrullinated. In some embodiments, the R in SEQ ID NO:1 is not citrullinated.

Also provided is a method of inducing an immune response in a human individual, the method comprising administering a sufficient amount of the composition as described above or elsewhere herein to the human individual, thereby inducing an immune response in the human individual to histone 3 variant H3.3 or H3.1. In some embodiments, the composition comprises an adjuvant selected from the group consisting of polyICLC and *Bacillus* Calmette-Guérin (BCG) vaccine. In some embodiments, the immune response is a cytotoxic T-cell response. In some embodiments, the human individual has a glioma. In some embodiments, the individual carries an HLA-*0201, HLA-*0202, HLA-*0203, HLA-*0204, HLA-*0205, HLA-*0206, HLA-*0207, or HLA-*0211 allele.

Also provided is an antibody that specifically binds to RMSAPSTGGV (SEQ ID NO:2) and does not bind to RKSAPSTGGV (SEQ ID NO:3). In some embodiments, the antibody is linked to a heterologous detectable label. In some embodiments, the label is fluorescent.

Also provided is a T-cell expressing one or more polypeptides comprising a T-cell receptor (TCR), or a peptide/MHC complex-binding fragment thereof or a peptide/HLA complex-binding fragment thereof, that binds the peptide as described above or elsewhere herein in a peptide/MHC complex or peptide/HLA complex. In some embodiments, the TCR is heterologous to the T-cell. In some embodiments, expression of the TCR is under the control of a heterologous promoter (e.g., as transgenes). In some embodiments, the TCR comprises one or more of the CDRs as listed in SEQ ID NOs:12-17, optionally in a heterologous framework region. The TCR will in general be formed of an alpha and a beta chain (two separate polypeptides). In some embodiments, the TCR comprises SEQ ID NO:8, SEQ ID NO:10, or both, either as a fusion protein or as separate proteins. In some embodiments, the TCR comprises complementarity determining regions (CDRs) as listed in SEQ ID NOs:12-17 (i.e., alpha chain CDR 1, 2, and 3 being SEQ ID NOs; 12, 13, and 14, respectively, and beta chain CDRs 1, 2, and 3 being SEQ ID NOs; 15, 16, and 17, respectively). In some embodiments, the glioma cell is a glioblastoma (GBM) cell. In some embodiments, the glioma cell is a diffuse intrinsic pontine glioma (DIPG) cell. In some embodiments, the glioma cell is a ependymoma, astrocytoma, oligodendroglioma, brainstem glioma, thalamic glioma, spinal cord glioma, or optic nerve glioma. In some embodiments, the TCR comprises a first polypeptide comprising a TCR alpha chain and a second polypeptide comprising a TCR beta chain.

Also provided is an isolated nucleic acid encoding an alpha chain, a beta chain, or both an alpha chain and a beta chain of the T-cell receptor (TCR) or a peptide/MHC complex-binding fragment thereof or a peptide/HLA complex-binding fragment thereof as described above or elsewhere herein. In some embodiments, the TCR comprises alpha chain complementarity determining region (CDR) 1, 2, and 3 being SEQ ID NOs; 12, 13, and 14, respectively, and beta chain CDRs 1, 2, and 3 being SEQ ID NOs; 15, 16, and 17, respectively.

Also provided is an expression cassette comprising a promoter operably linked to the nucleic acid as described above or elsewhere herein. In some embodiments, the promoter is heterologous to the nucleic acid.

Also provided is a method of targeting T-cells to cells (e.g., glioma cells) expressing histone 3 variant H3.3 or H3.1 in an individual in need thereof. In some embodiments, the method comprises, administering to the individual a T-cell expressing a polypeptide comprising a T-cell receptor (TCR), or a peptide/MHC complex binding fragment thereof or a peptide/HLA complex binding fragment thereof, that binds (R/A)MSAP(S/A)TGGV (SEQ ID NO:1) in a peptide/MHC complex or peptide/HLA complex, thereby targeting the T-cell to glioma cells expressing histone 3 variant H3.3 or H3.1. In some embodiments, the TCR is heterologous to the T-cell. In some embodiments, expression of the TCR is under the control of a heterologous promoter. In some embodiments, the TCR comprises complementarity determining regions (CDRs) as listed in SEQ ID NOs:12-17 (i.e., alpha chain CDR 1, 2, and 3 being SEQ ID NOs; 12, 13, and 14, respectively, and beta chain CDRs 1, 2, and 3 being SEQ ID NOs; 15, 16, and 17, respectively). In some embodiments, the glioma cell is a glioblastoma (GBM) cell. In some embodiments, the glioma cell is a diffuse intrinsic pontine glioma (DIPG) cell. In some embodiments, the glioma cell is a ependymoma, astrocytoma, oligodendroglioma, brainstem glioma, thalamic glioma, spinal cord glioma, or optic nerve glioma.

Also provided is a method of enriching for T-cells expressing a TCR that binds the peptide as described above or elsewhere herein. In some embodiments, the method comprises generating a starting culture of T-cells expressing TCRs; culturing the T-cells in the presence of the peptide to generate an enriched culture of T-cells, wherein the enriched culture is enriched for T-cells expressing TCRs that bind the peptide compared to the starting culture. In some embodiments, the culturing comprises culturing the T-cells in the presence of IL-2, IL-4, IL-7, IL-15, or combinations thereof. In some embodiments, the method further comprises sorting cells in the enriched culture for T-cells that bind the peptide in a peptide/MHC complex to form a further enriched population of T-cells expressing TCRs that bind the peptide/MHC complex. In some embodiments, the sorting comprises contacting cells in the enriched culture with a fluorochrome-conjugated peptide-major histocompatibility complex (pMHC) multimer.

DEFINITIONS

"Nucleic acid" refers to deoxyribonucleotides or ribonucleotides and polymers thereof in either single- or double-stranded form, and complements thereof. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

Unless otherwise indicated, a particular nucleic acid sequence also implicitly encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); Rossolini et al., *Mol. Cell. Probes* 8:91-98 (1994)).

The terms "polypeptide," "peptide" and "protein" are used interchangeably herein to refer to a polymer of amino acid residues. The terms encompass amino acid polymers in which one or more amino acid residue is an artificial chemical mimetic of a corresponding naturally occurring amino acid, as well as naturally occurring amino acid polymers and non-naturally occurring amino acid polymers.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. The term "amino acid analogs" refers to compounds that have the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. The term "amino acid mimetics" refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and UGG, which is ordinarily the only codon for tryptophan) can be modified to yield a functionally identical molecule. Accordingly, each silent variation of a nucleic acid which encodes a polypeptide is implicit in each described sequence with respect to the expression product, but not with respect to actual probe sequences.

For amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, *Proteins* (1984)).

A "label" or a "detectable moiety" is a composition detectable by spectroscopic, photochemical, biochemical, immunochemical, chemical, or other physical means. For example, useful labels include $^{32}P$, fluorescent dyes, electron-dense reagents, enzymes (e.g., as commonly used in an ELISA), biotin, digoxigenin, or haptens and proteins which can be made detectable, e.g., by incorporating a radiolabel into the peptide or used to detect antibodies specifically reactive with the peptide.

An antibody can consist of one or more polypeptides substantially encoded by immunoglobulin genes or fragments of immunoglobulin genes. The recognized immunoglobulin genes include the kappa, lambda, alpha, gamma, delta, epsilon and mu constant region genes, as well as myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. An "antibody" functions as a binding protein and is structurally defined as comprising an amino acid sequence from or derived from the framework region of an immunoglobulin-encoding gene of a vertebrate animal.

A typical immunoglobulin (antibody) structural unit is known to comprise a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

The term "antibody" as used herein encompasses antibody fragments that retain antigen-binding specificity. For example, there are a number of well characterized antibody fragments. Thus, for example, pepsin digests an antibody C-terminal to the disulfide linkages in the hinge region to produce F(ab)'2, a dimer of Fab which itself is a light chain joined to VH-CH1 by a disulfide bond. The F(ab)'2 may be reduced under mild conditions to break the disulfide linkage in the hinge region thereby converting the (Fab')2 dimer into an Fab' monomer. The Fab' monomer is essentially an Fab with part of the hinge region (see, e.g., Fundamental Immunology, W. E. Paul, ed., Raven Press, N.Y. (1993), for a more detailed description of other antibody fragments). While various antibody fragments are defined in terms of the digestion of an intact antibody, one of skill will appreciate that fragments can be synthesized de novo either chemically or by utilizing recombinant DNA methodology. Thus, the term antibody, as used herein also includes antibody fragments either produced by the modification or digestion of whole antibodies or synthesized using recombinant DNA methodologies.

Antibodies can include $V_H$-$V_L$ dimers, including single chain antibodies (antibodies that exist as a single polypeptide chain), such as single chain Fv antibodies (sFv or scFv) in which a variable heavy and a variable light region are joined together (directly or through a peptide linker) to form a continuous polypeptide. The single chain Fv antibody is a covalently linked $V_H$-$V_L$ which may be expressed from a nucleic acid including $V_H$- and $V_L$-encoding sequences either joined directly or joined by a peptide-encoding linker (e.g., Huston, et al. *Proc. Nat. Acad. Sci. USA*, 85:5879-5883, 1988). While the $V_H$ and $V_L$ are connected to each as a single polypeptide chain, the $V_H$ and $V_L$ domains associate non-covalently. Alternatively, the antibody can be another fragment. Other fragments can also be generated, e.g., using recombinant techniques, as soluble proteins or as fragments obtained from display methods. Antibodies can also include diantibodies and miniantibodies. Antibodies of the invention also include heavy chain dimers, such as antibodies from camelids. Thus, in some embodiments an antibody is dimeric. In other embodiments, the antibody may be in a monomeric form that has an active isotype. In some embodiments the antibody is in a multivalent form, e.g., a trivalent or tetravalent form.

As used herein, "complementarity-determining region (CDR)" refers to the three hypervariable regions in each chain that interrupt the four "framework" regions established by the light and heavy chain variable regions. The CDRs are primarily responsible for binding to an epitope of an antigen. The CDRs of each chain are typically referred to as CDR1, CDR2, and CDR3, numbered sequentially starting from the N-terminus, and are also typically identified by the chain in which the particular CDR is located. Thus, a $V_H$ CDR3 is located in the variable domain of the heavy chain of the antibody in which it is found, whereas a $V_L$ CDR1 is the CDR1 from the variable domain of the light chain of the antibody in which it is found.

As used herein, "V-region" refers to an antibody variable region domain comprising the segments of Framework 1, CDR1, Framework 2, CDR2, and Framework3, including CDR3 and Framework 4, which segments are added to the V-segment as a consequence of rearrangement of the heavy chain and light chain V-region genes during B-cell differentiation.

The sequences of the framework regions of different light or heavy chains are relatively conserved within a species. The framework region of an antibody, that is the combined framework regions of the constituent light and heavy chains, serves to position and align the CDRs in three dimensional space.

The amino acid sequences of the CDRs and framework regions can be determined using various well known definitions in the art, e.g., Kabat, Chothia, international ImMunoGeneTics database (IMGT), and AbM (see, e.g., Johnson et al., supra; Chothia & Lesk, 1987, Canonical structures for the hypervariable regions of immunoglobulins. *J. Mol. Biol.* 196, 901-917; Chothia C. et al., 1989, Conformations of immunoglobulin hypervariable regions. Nature 342, 877-883; Chothia C. et al., 1992, structural repertoire of the human VH segments J. Mol. Biol. 227, 799-817; Al-Lazikani et al., *J. Mol. Biol* 1997, 273(4)). Definitions of antigen combining sites are also described in the following: Ruiz et al., IMGT, the international ImMunoGeneTics database. *Nucleic Acids Res.*, 28, 219-221 (2000); and Lefranc, M.-P. IMGT, the international ImMunoGeneTics database. *Nucleic Acids Res*. January 1; 29(1):207-9 (2001); MacCallum et al, Antibody-antigen interactions: Contact analysis and binding site topography, *J. Mol. Biol.*, 262 (5), 732-745 (1996); and Martin et al, *Proc. Natl Acad. Sci. USA*, 86, 9268-9272 (1989); Martin, et al, *Methods Enzymol.*, 203, 121-153, (1991); Pedersen et al, *Immunomethods*, 1, 126, (1992); and Rees et al, In Sternberg M. J. E. (ed.), Protein Structure Prediction. Oxford University Press, Oxford, 141-172 1996).

"Epitope" or "antigenic determinant" refers to a site on an antigen to which an antibody binds. Epitopes can be formed both from contiguous amino acids or noncontiguous amino acids juxtaposed by tertiary folding of a protein. Epitopes formed from contiguous amino acids are typically retained on exposure to denaturing solvents whereas epitopes formed by tertiary folding are typically lost on treatment with denaturing solvents. An epitope typically includes at least 3, and more usually, at least 5 or 8-10 amino acids in a unique spatial conformation. Methods of determining spatial conformation of epitopes include, for example, x-ray crystallography and 2-dimensional nuclear magnetic resonance. See, e.g., Epitope Mapping Protocols in Methods in Molecular Biology, Vol. 66, Glenn E. Morris, Ed (1996).

As used herein, "chimeric antibody" refers to an immunoglobulin molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region, or portion thereof, having a different or altered antigen specificity; or with corresponding sequences from another species or from another antibody class or subclass.

The phrase "specifically (or selectively) binds" to an antibody or "specifically (or selectively) immunoreactive with," when referring to a protein or peptide, refers to a binding reaction that is determinative of the presence of the protein, often in a heterogeneous population of proteins and other biologics such as a mixture of cells or a cell lysate. Thus, under designated immunoassay conditions, the specified antibodies bind to a particular protein (e.g., SEQ ID NO:2) at least two times the background and more typically more than 10 to 100 times background. Specific binding to an antibody under such conditions requires an antibody that is selected for its specificity for a particular protein. For example, polyclonal antibodies can be selected to obtain only those polyclonal antibodies that are specifically immunoreactive with the selected antigen and not with other proteins. This selection may be achieved by subtracting out antibodies that cross-react with other molecules. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, *Using Antibodies, A Laboratory Manual* (1998) for a description of immunoassay formats and conditions that can be used to determine specific immunoreactivity).

"Antigen presenting cells", or "APCs" are cells that cells that mediate the cellular immune response by processing and presenting antigens to the T-cell receptor and include Langerhans cells, veiled cells of afferent lymphatics, dendritic cells and interdigitating cells of lymphoid organs. APCs include mononuclear cells such as lymphocytes and macrophages.

A polynucleotide or polypeptide sequence is "heterologous" to an organism or a second polynucleotide sequence if it originates from a foreign species, or, if from the same species, is modified from its original form. For example, when a heterologous promoter is said to be operably linked to a coding sequence, it means that the coding sequence is derived from one species whereas the promoter sequence is derived from another, different species; or, if both are derived from the same species, the coding sequence is not naturally associated with the promoter (e.g., the promoter is a genetically engineered promoter or promoter fragment not found naturally associated with the coding sequence).

BRIEF DESCRIPTION OF THE DRAWINGS

FIG. 6A-C. Evaluation of H3.3.K27M-specific TCR. (6A), J.RT-T3.5 cells were transduced with lentiviral vector encoding the TCR α- or β-chains derived from H3.3.K27M-specific CTL clone IH5 (J.RT-T3.5-TCR). The J.RT-T3.5-TCR or control non-transduced J.RT-T3.5 cells were evaluated for the surface TCR expression using PE-labeled HLA-A*0201/H3.3.K27M tetramer (upper panel) or PE-labeled anti-CD3 mAb (lower panel) and FITC-labeled anti-human CD8 mAb (upper and lower panels). Since J.RT3-T3.5 cells are CD4+ and CD8-negative, tetramer+ CD8-negative cells are ones expressing the transgene-derived TCR. CD3-upregulation indicates activation of cells. (6B), J.RT-T3.5-TCR, but not control J.RT-T3.5 cells, upregulate CD69 expression upon recognition of the H3.3 K27M peptide loaded on T2 cells. (3C), DIPG 13 cells [HLA-A*0201+ (albeit dim), K27M mutation+] were incubated with J.RT-T3.5-TCR or control J.RT-T3.5 cells. IL-2 secretion in the culture media was assayed by specific ELISA.

FIG. 7. Expression of transgene-derived TCR. J.RT3-T3.5 cells, which are deficient for endogenous TCR β-chain, were transduced with lentiviral vectors (pHIV-mH3TCR-IRES-Luc or pMP270-mH3TCR) encoding TCR α- and β-chains derived from an H3.3.K27M-specific CTL clone (IH5; FIG. 5) and evaluated for the surface TCR expression using PE-labeled HLA-A2/H3.3.K27M tetramer and FITC-labeled anti-human CD8 mAb. Since J.RT3-T3.5 cells are CD4+ and CD8-negative, tetramer+ CD8-negative cells are ones expressing the transgene-derived TCR. Negative control cells are non-transfected cells stained with the same tetramer indicting the specificity of the tetramer-binding.

DETAILED DESCRIPTION OF THE INVENTION

Introduction

Figure 1:
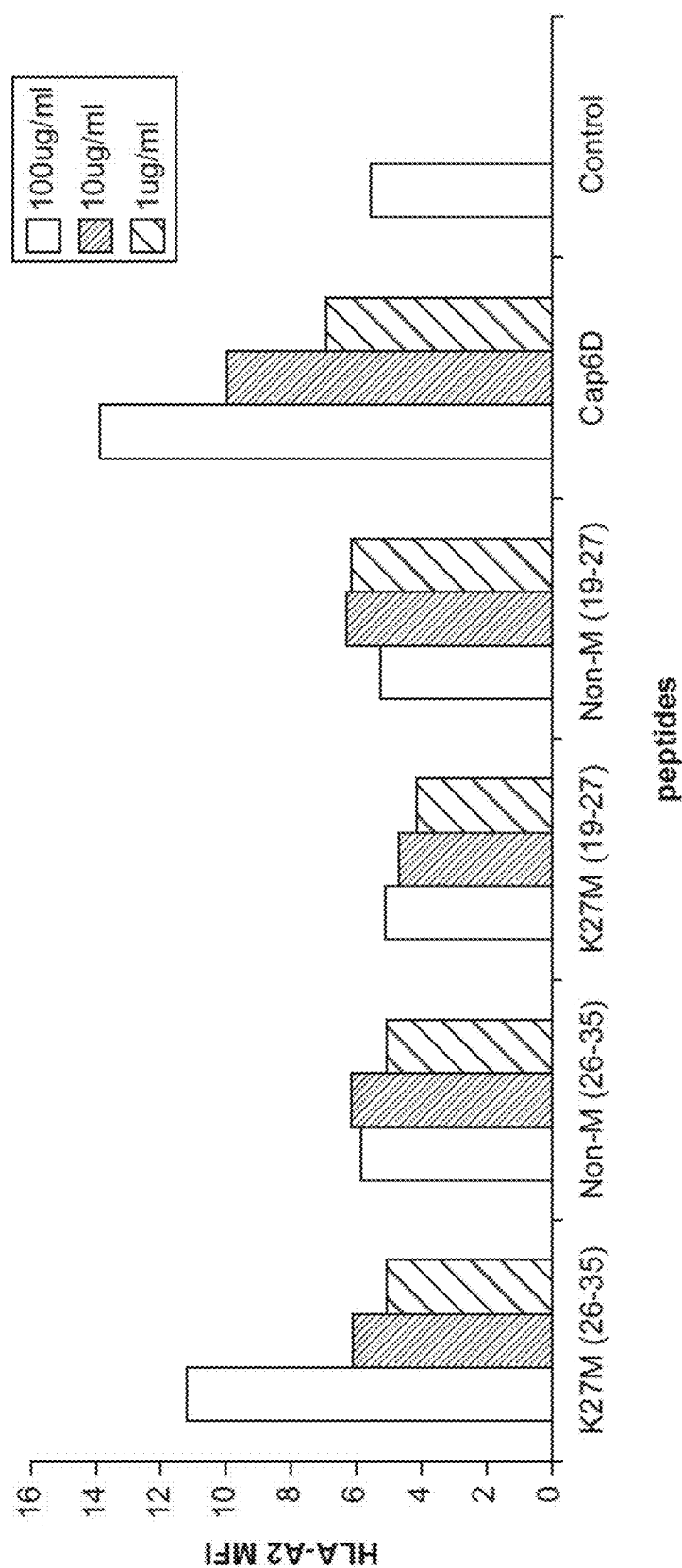
FIG. 1. Identification of a HLA-A*0201-restricted epitope in H3.3 with the K27M mutation. A. HLA-A201 binding ability of H3.3-derived peptides was analyzed by T2 cell A2-binding assay. Capt-6D is an altered peptide ligand, which has been derived from an epitope in human carcinoembryonic Ag, CEA605-613 and was used as positive control. B. H3.3 tetramer staining analysis of the CD8+ CTLs generated with the H3.3.K27M (26-35) after 1st antigen stimulation (left) and weekly re-stimulations (right).

The inventors have found that a peptide that encompasses amino-acid positions 26-35 of H3.3, which includes the K27M mutation [referred to herein as "H3.3.K27M (26-35)"], can induce specific cytotoxic T lymphocyte (CTL) responses in human leukocyte antigen (HLA)-A2+ donors. Furthermore, CTLs against H3.3.K27M (26-35) recognize HLA-A2+ glioma cell lines that also harbor the K27M mutation. Accordingly, provided herein are compositions for use in generating an immune response in human subjects to a peptide comprising amino-acid positions of 26-35 of H3.3 or variants thereof.

CTL Peptides

The CTL peptides described herein comprise (R/A)MSAP(S/A)TGGV (SEQ ID NO:1), where the amino acid options in parentheses are alternative options for the specified position. Accordingly, CTL peptides can comprise RMSAPSTGGV (SEQ ID NO:2), AMSAPSTGGV (SEQ ID NO:5), RMSAPATGGV (SEQ ID NO:6), or AMSAPATGGV (SEQ ID NO:7). CTL peptides comprising RMSAPSTGGV (SEQ ID NO:2) or AMSAPSTGGV (SEQ ID NO:5) represent peptides for targeting H3.3.K27M (26-35). CTL peptides comprising RMSAPATGGV (SEQ ID NO:6), or AMSAPATGGV (SEQ ID NO:7) represent peptides for targeting the corresponding H3.1 K27M (26-35). The length of the CTL peptides can vary so long as the peptides are effective at inducing an immune response, e.g., a CTL response. In some embodiments, the peptide will consist of 100 or fewer or 50 or fewer amino acids. In some embodiments, the CTL peptides will have 10-14 amino acids, i.e., will be 10, 11, 12, 13, or 14 amino acids long. As SEQ ID NO:1 is 10 amino acids long, the 11 or 14-amino acid options will have one to four additional amino acids on the amino or carboxyl terminus of SEQ ID NO:1, or in some embodiments, one or two additional amino acid on each of the amino and carboxyl terminus of SEQ ID NO:1. Additional amino acids can be selected from any of the twenty naturally-occurring amino acids or can be a non-naturally-occurring amino acid.

The peptides can be modified to alter, for example, their in vivo stability. For instance, inclusion of one or more D-amino acids in the peptide typically increases stability, particularly if the D-amino acid residues are substituted at one or both termini of the peptide sequence. Stability can be assayed in a variety of ways such as by measuring the half-life of the proteins during incubation with peptidases or human plasma or serum. A number of such protein stability assays have been described (see, e.g., Verhoef et al., *Eur. J. Drug Metab. Pharmacokin.* 11:291-302 (1986)).

The peptides can also be modified by linkage to other molecules. For example, different N- or C-terminal groups may be introduced to alter the molecule's physical and/or chemical properties. Such alterations may be utilized to affect, for example, adhesion, stability, bioavailability, localization or detection of the molecules. For diagnostic purposes, a wide variety of labels may be linked to the terminus, which may provide, directly or indirectly, a detectable signal. Thus, the peptides of the subject invention may be modified in a variety of ways for a variety of end purposes while still retaining biological activity.

The following examples of chemical derivatives are provided by way of illustration and not by way of limitation.

Aromatic amino acids may be replaced with D- or L-naphylalanine, D- or L-Phenylglycine, D- or L-2-thieneylalanine, D- or L-1-, 2-, 3- or 4-pyreneylalanine, D- or L-3-thieneylalanine, D- or L-(2-pyridinyl)-alanine, D- or L-(3-pyridinyl)-alanine, D- or L-(2-pyrazinyl)-alanine, D- or L-(4-isopropyl)-phenylglycine, D-(trifluoromethyl)-phenyl-glycine, D-(trifluoromethyl)-phenylalanine, D-p-fluoro-phenylalanine, D- or L-p-biphenylphenyl alanine, D- or L-p-methoxybiphenylphenylalanine, D- or L-2-indole-(alkyl)alanines, and D- or L-alkylamines where alkyl may be substituted or unsubstituted methyl, ethyl, propyl, hexyl, butyl, pentyl, iso-propyl, iso-butyl, sec-isotyl, iso-pentyl, non-acidic amino acids, of C1-C20.

Acidic amino acids can be substituted with non-carboxylate amino acids while maintaining a negative charge, and derivatives or analogs thereof, such as the non-limiting examples of (phosphono)-alanine, glycine, leucine, isoleucine, threonine, or serine; or sulfated (e.g., —SO$_3$H) threonine, serine, tyrosine.

Other substitutions may include unnatural hyroxylated amino acids made by combining "alkyl" (as defined and exemplified herein) with any natural amino acid. Basic amino acids may be substituted with alkyl groups at any position of the naturally occurring amino acids lysine, arginine, ornithine, citrulline, or (guanidino)-acetic acid, or other (guanidino) alkyl-acetic acids, where "alkyl" is define as above. Nitrile derivatives (e.g., containing the CN-moiety in place of COOH) may also be substituted for asparagine or glutamine, and methionine sulfoxide may be substituted for methionine. Methods of preparation of such peptide derivatives are well known to one skilled in the art.

In addition, any amide linkage can be replaced by a ketomethylene moiety, e.g., (—C(=O)—CH$_2$—) for (—(C=O)—NH—). Such derivatives are expected to have the property of increased stability to degradation by enzymes, and therefore possess advantages for the formulation of compounds which may have increased in vivo half-lives, as administered by oral, intravenous, intramuscular, intraperitoneal, topical, rectal, intraocular, or other routes.

In addition, any amino acid can be replaced by the same amino acid but of the opposite chirality. Thus, any amino acid naturally occurring in the L-configuration (which may also be referred to as the R or S configuration, depending upon the structure of the chemical entity) may be replaced with an amino acid of the same chemical structural type, but of the opposite chirality, generally referred to as the D-amino acid but which can additionally be referred to as the R- or the S-, depending upon its composition and chemical configuration. Such derivatives have the property of greatly increased stability to degradation by enzymes, and therefore are advantageous in the formulation of compounds which may have longer in vivo half-lives, when administered by oral, intravenous, intramuscular, intraperitoneal, topical, rectal, intraocular, or other routes.

Fusion peptides including an antigenic peptide as described above fused to another peptide sequence are specifically contemplated for use with the methods and compositions described herein. In some embodiments, peptides include fusion peptides composed of a CTL sequence as described herein (e.g., SEQ ID NO:1) and a helper T lymphocyte (CD4) epitope sequence fused together. Examples of suitable CD4 epitopes include the synthetic sequence PADRE, tetanus-specific peptides, peptides derived from the same antigen or other antigens from the virus that is to be targeted. Similarly, for cancer antigens, a CD4 peptide derived from the same antigen, or any other cell-antigen known in the art, and the like may be used. Linker peptide sequences at the N- or C-terminal end of the fusion or between the CTL and CD4 epitopes in the fusion also may be used. Such linker sequences generally can be, for example, from about 1 to about 10 amino acids in length and, e.g., about 2 to about 7 amino acids or from about 3 to about 5 amino acids in length can optionally comprise modified or non-traditional amino acids.

Also provided are peptide/HLA-A2 multimers, and in some embodiments, their use to isolate peptide-specific CTLs. "Multimers" include, e.g., tetramers, pentamers and any number of MHC-peptide structure assembled around the core molecule with fluorochrome. In some embodiments, the selected MHC molecules (e.g., HLA-A2) along with beta2-microgloblin are assembled around one core molecule which connects a fluorochrome molecule (such as FITC, so that the multimer will fluoresce) and multiple MHC-beta-microgloblin molecules (in case of tetramer and pentamer, there will be 4 and 5, respectively). Then, the MHC molecule is also bound with the peptide so that the MHC-peptide complex on the multimer molecule can be recognized by the TCR on T-cells. See, e.g., Wooldridge, et al., *Immunology* 126(2): 147-164 (2009); Yokouchi, et al., *Cancer Sci.* 97(2):148-54 (2006). Accordingly, in some embodiments, fluorochrome-conjugated peptide-major histocompatibility complex (pMHC) multimers, wherein the peptide is a CTL peptide (e.g., comprising SEQ ID NO:1) are provided.

In some embodiments, T-cell populations are enriched for T-cells expressing one or more TCRs that bind to the CTL peptide/MHC complex. For example, in some embodiments, a T-cell population is cultured in the presence of the CTL peptide (either the naked peptide or peptide loaded onto APCs), thereby preferentially stimulating division of T-cells carrying TCRs that bind the peptide/MHC complex. In some embodiments, the culturing occurs in the presence of IL-2, IL-4, IL-7 or IL-15 alone, or of 2-way, 3-way, or 4-way combinations thereof. T-cell populations expanded in this way will be enriched for TCRs that bind the protein/MHC complex. Subsequently, fluorochrome-conjugated peptide-major histocompatibility complex (pMHC) multimers can be used to label the T-cells expressing the TCRs that bind the peptide/MHC complex, and can be sorted, for example by FACS.

Exemplary TCR alpha and beta chain sequences that recognize the H3.3.K27M epitope are provided below with CDR1, CDR2, and CDR3 underlined.

```
TCRA-Va19*01/J43
                                       (SEQ ID NO: 8)
Met L T A S L L R A V I A S I C V V S S Met A Q K

V T Q A Q T E I S V V E K E D V T L D C V Y E

T R D T T Y Y L F W Y K Q P P S G E L V F L I R

R N S F D E Q N E I S G R Y S W N F Q K S T S S F

N F T I T A S Q V V D S A V Y F C A L S E E N D

Met R F G A G T R L T V K P N I Q N P D P A V Y Q

L R D S K S S D K S V C L F T D F D S Q T N V S Q

S K D S D V Y I T D K T V L D Met R S Met D F K S

N S A V A W S N K S D F A C A N A F N N S I I P E
```

```
D T F F P S P E S S C D V K L V E K S F E T D T N

L N F Q N L S V I G F R I L L L K V A G F N L L

Met T L R L W S S Stop
```

(SEQ ID NO: 12)
CDR1: T R D T T Y Y;

(SEQ ID NO: 13)
CDR2: R N S F (SEQ ID NO: 14)
CDR3: A L S E
Coding sequence of the above amino acid sequence:
(SEQ ID NO: 9)

```
ATGCTGACTGCCAGCCTGTTGAGGGCAGTCATAGCCTCCATCTGTGTTGT

ATCCAGCATGGCTCAGAAGGTAACTCAAGCGCAGACTGAAATTTCTGTGG

TGGAGAAGGAGGATGTGACCTTGGACTGTGTGTATGAAACCCGTGATACT

ACTTATTACTTATTCTGGTACAAGCAACCACCAAGTGGAGAATTGGTTTT

CCTTATTCGTCGGAACTCTTTTGATGAGCAAAATGAAATAAGTGGTCGGT

ATTCTTGGAACTTCCAGAAATCCACCAGTTCCTTCAACTTCACCATCACA

GCCTCACAAGTCGTGGACTCAGCAGTATACTTCTGTGCTCTGAGTGAGGA

GAATGACATGCGCTTTGGAGCAGGGACCAGACTGACAGTAAAACCAAATA

TCCAGAACCCTGACCCTGCCGTGTACCAGCTGAGAGACTCTAAATCCAGT

GACAAGTCTGTCTGCCTATTCACCGATTTTGATTCTCAAACAAATGTGTC

ACAAAGTAAGGATTCTGATGTGTATATCACAGACAAAACTGTGCTAGACA

TGAGGTCTATGGACTTCAAGAGCAACAGTGCTGTGGCCTGGAGCAACAAA

TCTGACTTTGCATGTGCAAACGCCTTCAACAACAGCATTATTCCAGAAGA

CACCTTCTTCCCCAGCCCAGAAAGTTCCTGTGATGTCAAGCTGGTCGAGA

AAAGCTTTGAAACAGATACGAACCTAAACTTTCAAAACCTGTCAGTGATT

GGGTTCCGAATCCTCCTCCTGAAAGTGGCCGGGTTTAATCTGCTCATGAC

GCTGCGGCTGTGGTCCAGCTGA
```

TCRB-Vb27/J2.7
(SEQ ID NO: 10)
```
Met G P Q L L G Y V V L C L L G A G P L E A Q V T

Q N P R Y L I T V T G K K L T V T C S Q

N Met N H E Y Met S W Y R Q D P G L G L R Q I Y

Y S Met N V E V T D K G D V P E G Y K V S R K E K

R N F P L I L E S P N P N Q T S L Y F

C A S G W G G P F Y E Q Y F G P G T R L T V T E D

L K N V F P P E V A V F E P S E A E I S H T Q K A

T L V C L A T G F Y P D H V E L S W W V N G K E V

H S G V S T D P Q P L K E Q P A L N D S R Y C L S

S R L R V S A T F W Q N P R N H F R C Q V Q F Y G

L S E N D E W T Q D R A K P V T Q I V S A E A W G

R A D C G F T S E S Y Q Q G V L S A T I L Y E I L

L G K A T L Y A V L V S A L V L Met A Met V K R K

D S R G Stop
```

(SEQ ID NO: 15)
CDR1: N Met N H E Y;

(SEQ ID NO: 16)
CDR2: Y S Met N V E V T (SEQ ID NO: 17)
CDR3: C A S G W G G P F Y E Q Y
Coding sequence of the above amino acid sequence:
(SEQ ID NO: 11)

```
ATGGGCCCCCAGCTCCTTGGCTATGTGGTCCTTTGCCTTCTAGGAGCAGG

CCCCCTGGAAGCCCAAGTGACCCAGAACCCAAGATACCTCATCACAGTGA

CTGGAAAGAAGTTAACAGTGACTTGTTCTCAGAATATGAACCATGAGTAT

ATGTCCTGGTATCGACAAGACCCAGGGCTGGGCTTAAGGCAGATCTACTA

TTCAATGAATGTTGAGGTGACTGATAAGGGAGATGTTCCTGAAGGGTACA

AAGTCTCTCGAAAAGAGAAGAGGAATTTCCCCCTGATCCTGGAGTCGCCC

AACCCCAACCAGACCTCTCTGTACTTCTGTGCCAGCGGCTGGGGTGGTCC

ATTCTACGAGCAGTACTTCGGGCCGGGCACCAGGCTCACGGTCACAGAGG

ACCTGAAAAACGTGTTCCCACCCGAGGTCGCTGTGTTTGAGCCATCAGAA

GCAGAGATCTCCCACACCCAAAAGGCCACACTGGTATGCCTGGCCACAGG

CTTCTACCCCGACCACGTGGAGCTGAGCTGGTGGGTGAATGGGAAGGAGG

TGCACAGTGGGGTCAGCACAGACCCGCAGCCCCTCAAGGAGCAGCCCGCC

CTCAATGACTCCAGATACTGCCTGAGCAGCCGCCTGAGGGTCTCGGCCAC

CTTCTGGCAGAACCCCCGCAACCACTTCCGCTGTCAAGTCCAGTTCTACG

GGCTCTCGGAGAATGACGAGTGGACCCAGGATAGGGCCAAACCCGTCACC

CAGATCGTCAGCGCCGAGGCCTGGGGTAGAGCAGACTGTGGCTTCACCTC

CGAGTCTTACCAGCAAGGGGTCCTGTCTGCCACCATCCTCTATGAGATCT

TGCTAGGGAAGGCCACCTTGTATGCCGTGCTGGTCAGTGCCCTCGTGCTG

ATGGCCATGGTCAAGAGAAAGGATTCCAGAGGCTAG
```

In some embodiments, one or more T-cells expressing TCR alpha and beta chain sequences that recognize the H3.3.K27M epitope (e.g., as presented in an antigen presenting cell in the context of an MHC/HLA protein) are administered to an individual (e.g., a human). In some embodiments, the individual has one or more cells that express the H3.3.K27M epitope and the T-cell is administered to contact the cell expressing the epitope. In some embodiments, the T-cell, once in contact with the cell expressing the epitope, directly or indirectly kills the cell. In some embodiments, the cell expressing the epitope is a glioma cell. In some embodiments, the glioma cell is a glioblastoma (GBM) cell. In some embodiments, the glioma cell is a diffuse intrinsic pontine glioma (DIPG) cell. In some embodiments, the glioma cell is an ependymoma, astrocytoma, oligodendroglioma, brainstem glioma, thalamic glioma, spinal cord glioma, or optic nerve glioma. In some embodiments, the T-cells are administered intracranially or intravenously.

In some embodiments, the T-cell is a primary or expanded T-cell. In some embodiments, the T-cells are CD4+ T-cells or CD8 T-cells. In some embodiments, the T-cell is from the individual into which an expression cassette encoding the TCR or part thereof has been introduced so that the T-cell expresses the TCR on the surface of the T-cell. Methods of generating T-cells expressing heterologous genes and methods of administering T-cells are described in, for example, US Patent Publications 2017/0067021 and 2016/0120905.

Polynucleotides

Polynucleotides encoding the CTL peptides described herein are provided and are referred to as "CTL polynucleotides". In some embodiments, the CTL polynucleotides can be a DNA or RNA sequence. The CTL polynucleotide is can be operably linked to some or all of transcriptional and translational regulatory elements, such as a promoter, enhancer and polyadenylation sequence. Regulatory sequences are art-recognized and are described, e.g., in Goeddel; *Gene Expression Technology: Methods in Enzymology* 185, Academic Press, San Diego, Calif. (1990). In some embodiments, the promoter is a constitutive promoter, e.g., a strong viral promoter, e.g., CMV promoter. The promoter can also be cell- or tissue-specific, that permits substantial transcription of the DNA only in predetermined cells, e.g., in antigen presenting cells, such as the dendritic cell-specific CD1 lc promoter described in Brocker T, J. Leuk. *Biology* 66:331-335, 1999. The promoter can also be an inducible promoter, for example, a metallothionein promoter. Other inducible promoters include those that are controlled by the inducible binding, or activation, of a transcription factor, e.g., as described in U.S. Pat. Nos. 5,869,337 and 5,830,462 by Crabtree et al., describing small molecule inducible gene expression (a genetic switch); International patent applications PCT/US94/01617, PCT/US95/10591, PCT/US96/09948 and the like, as well as in other heterologous transcription systems such as those involving tetracyclin-based regulation reported by Bujard et al., generally referred to as an allosteric "off-switch" described by Gossen and Bujard, *Proc. Natl. Acad. Sci. U.S.A.* (1992) 89:5547 and in U.S. Pat. Nos. 5,464,758; 5,650,298; and 5,589,362 by Bujard et al. Other inducible transcription systems involve steroid or other hormone-based regulation.

The CTL polynucleotides may also be produced in part or in total by chemical synthesis, e.g., by the phosphoramidite method described by Beaucage and Carruthers, *Tetra. Letts.*, 22:1859-1862 (1981) or the triester method according to the method described by Matteucci et al., *J. Am. Chem. Soc*, 103:3185 (1981), and may be performed on commercial automated oligonucleotide synthesizers. A double-stranded fragment may be obtained from the single-stranded product of chemical synthesis either by synthesizing the complementary strand and annealing the strand together under appropriate conditions or by adding the complementary strand using DNA polymerase with an appropriate primer sequence.

The CTL polynucleotide operably linked to all necessary transcriptional and translational regulation elements can be injected as naked DNA into a subject or contacted in vitro with antigen presenting cells. In some embodiments, the CTL polynucleotide and regulatory elements are present in a plasmid or vector. Thus, the CTL polynucleotide can be DNA, which is itself non-replicating, but is inserted into a plasmid, which may further comprise a replicator. The DNA can be a sequence engineered so as not to integrate into the host cell genome. Exemplary vectors are expression vectors, i.e., vectors that allow expression of a nucleic acid in a cell. Exemplary expression vectors are those which contain both prokaryotic sequences, to facilitate the propagation of the vector in bacteria, and one or more eukaryotic transcription units that are expressed in eukaryotic cells.

Alternatively, derivatives of viruses such as the bovine papillomaviras (BPV-1), of Epstein-Barr virus (pHEBo, pREP-derived and p205) can be used for transient expression of proteins in eukaryotic cells. These viruses expressing the CTL polypeptides can be used to infect APCs, which are then administered to patients. For other suitable expression systems for both prokaryotic and eukaryotic cells, as well as general recombinant procedures, see Molecular Cloning: A Laboratory Manual, 2nd Ed., ed. by Sambrook, Fritsch and Maniatis (Cold Spring Harbor Laboratory Press: 1989), Chapters 16 and 17.

In some embodiments, the CTL polynucleotide is expressed in a prokaryote. In some embodiments, the polypeptide is expressed in *E. coli*. In some embodiments, the CTL polypeptide is expressed in *Listeria monocytogenes*, which in some embodiments, is attenuated, and which can be administered to a human individual to provide the CTL peptide to the individual. See, e.g., US Patent Publication No. US2013/0259891. In other embodiments, the CTL polynucleotide is expressed in a eukaryotic cell. For example, the CTL polynucleotide and polypeptide can be expressed in yeast, insect cells, animal cells, including mammalian cells, e.g., human cells.

Inducing an Immune Response

The CTL peptides of the invention are capable of inducing an immune response when administered to an animal (e.g., a human). An exemplary immune response is a CTL response. The CTL peptides, once introduced can be processed and presented to the MHC class I complex of an antigen presenting cell. Human MHC class I complex includes HLA-A, B, and C alleles. The CTL peptides (e.g., SEQ ID NO:1) have higher affinity to HLA-A2+ individuals. See Table 1. The MHC class I-bound epitope is then transported to the cell surface and recognized by cytotoxic T lymphocytes (CTLs) through T cell receptors (TCRs) located on their surface. Recognition of an antigen/MHC complex by the TCR triggers a cascade of protein and cytokine interactions leading to, among other interactions, the activation, maturation and proliferation of the precursor CTLs, resulting in CTL clones capable of destroying the cells exhibiting CTL peptides recognized as foreign.

In one embodiment, one or more CTL peptides as described herein are administered to the patient. In another embodiment, one or more polynucleotides encoding one or more CTLs are introduced to APCs, and these APCs expressing CTLs are administered into a human patient to induce an immune response, the cytotoxic T cell response. In some embodiments, the CTL peptides are loaded onto the APCs without expressing the CTL peptides in the cell. See, e.g., U.S. Pat. No. 8,652,462. In some embodiments, the APCs are harvested from an individual, loaded with the CTL peptides (or the CTL polynucleotides are introduced into the APCs), and then the APCs are introduced back into the individual (i.e., the cells are autologous) and a CTL immune response is induced in the individual to the CTL polypeptide.

In one embodiment, an immune response is induced by directly administering the CTL peptides to patients. Adjuvants and/or nonspecific inflammatory mediators are not required, but can be optionally administered with the active ingredient before, during, or after the priming and/or boosting of the immune response. Adjuvants are substances that are used to specifically or nonspecifically potentiate an antigen-specific immune response, perhaps through activation of antigen presenting cells. The adjuvant can be, e.g., Montanide-ISA 51 (e.g., from Seppic Hiltonol (e.g., from Oncovir), anti-CD40 agonistic monoclonal antibodies, polyICLC, *Bacillus* Calmette-Guérin (BCG) vaccine, an ADP-ribosylating exotoxin (e.g., cholera toxin, diphtheria toxin, *E. coli* heat-labile enterotoxin, pertussis toxin, *P. aeruginosa* exotoxin A), a fragment thereof containing the A and/or B subunit, a chemically modified or genetically mutated derivative thereof, or a derivative thereof with reduced toxicity; a chemical conjugate or genetic recombinant containing a bacterial ADP-ribosylating exotoxin or derivative thereof; a chemokine (e.g., defensins, HCC-1, HCC-4, MCP-1 MCP-3, MCP-4, MLP-1α, M1P-1β, M1P-1γ, MIP-3α, MIP-2, RANTES); another ligand of a chemokine receptor (e.g., CCR1, CCR-2, CCR-5, CCR-6, CXCR-1); a cytokine (e.g., IL-1β, IL-2, IL-6, IL-8, IL-10, IL-12; IFN-γ; TNF-α; GM-CSF); another ligand of a cytokine receptor; a salt (e.g., aluminum hydroxide or phosphate, calcium phosphate); lipid A or a derivative thereof (e.g., monophosphoryl or diphosphoryl lipid A, lipid A analogs, AGP, ASO2, ASO4, DC-Choi, Detox, OM-174); a pathogen-associated molecular pattern (PAMP); immunostimulatory CpG motifs in bacterial DNA or an oligonucleotide (see, for example, U.S. Pat. No. 6,218,371); a *Leishmania* homolog of eIF4a or a derivative thereof (see, for example, U.S. Pat. No. 5,876,735); a heat shock protein or derivative thereof; C3d tandem array; a muramyl dipeptide (MDP) or a derivative thereof (e.g., murabutide, threonyl-MDP, muramyl tripeptide); ISCOMS and saponins (e.g., Quil A, QS-21); squalene; superantigens; a ligand of a toll-like receptor, or the like. Adjuvants may be chosen to preferentially induce antibody or cellular effectors, specific antibody isotypes (e.g., IgM, IgD, IgA1, IgA2, secretory IgA, IgE, IgG1, IgG2, IgG3, and/or IgG4), or specific T-cell subsets (e.g., CTL, Th1, Th2 and/or TDTH)—For example, antigen presenting cells may present Class Il-restricted antigen to precursor CD4+ T cells, and the Th1 or Th2 pathway may be entered.

In another embodiment, the invention provides a method of administering APC cells expressing and/or presenting CTL peptides to induce immune response. Methods for delivering CTL polynucleotide to APCs are well-known in the art, for example, retroviruses, adenoviruses, lentiviruses, adeno-associated virus (AAV), and herpes simplex virus-1, vaccinia viruses, and canarypox or fowlpox viruses can infect APC. Most of these vectors cause transient gene expression lasting less than two weeks (Bonnet et al, 2000). To initiate an immune response, expression of peptides, proteins, or MHC molecules may only need to last about three to ten days (see, e.g., U.S. Pat. Nos. 5,656,465 and 5,833,975). Plasmids may also be used to transfer a gene into the cell by itself or with chemicals that enhance transfection, or via carriers. For example, cationic lipids, calcium phosphate, DEAE-dextran, polybrene-DMSO, or polycation amino acids (e.g., polylysine) are chemical transfectants.

The method may further involve a targeting molecule that preferentially binds to a target cell, for example antigen presenting cells. Such targeting mechanisms may include terminal galactosyl residues binding to asialoglycoprotein receptor (e.g., galactosylated nucleic acid and/or antigen), high-mannose oligosaccharide binding to mannose receptor (e.g., mannosylated nucleic acid and/or antigen), ligand binding to an Fc receptor (e.g., nucleic acid and/or antigen fused or linked to IgG constant region or other ligand of CD64), or membrane proteins highly expressed on antigen presenting cells (e.g., nucleic acid and/or antigen fused or linked to ligand or antibody specific for the membrane protein). Mannose receptors are exemplary targets because they are highly expressed on dendritic cells (especially Langerhans cells), and involved in antigen uptake. This significantly increases the APC's ability to capture exogenous proteins and process them (Sallusto, 1995). Antigen may be delivered to phagocytic cells of the skin such as, for example, Langerhans cells, other dendritic cells, macrophages, and other antigen presenting cells in the epidermis and dermis; antigen may also be delivered to phagocytic cells of the liver, spleen, and bone marrow that are known to serve as the antigen presenting cells through the blood stream or lymphatic system.

In a further embodiment, the composition can comprise the CTL polypeptide and also comprise the universal T cell epitope called PADRE® (Epimmune, San Diego; described, for example in U.S. Pat. No. 5,736,142 or International Application WO95/07707, which are enclosed herein by reference). A "PanDR binding peptide" or "PADRE® peptide" is a member of a family of molecules that binds more than one HLA class II DR molecule. The pattern that defines the PADRE® family of molecules can be thought of as an HLA Class U supermotif PADRE® binds to most HLA-DR molecules and stimulates in vitro and in vivo human helper T lymphocyte (HTL) responses. Alternatively, T-helper epitopes can be used from universally used vaccines such as tetanus toxoid.

Typically, a vaccine or vaccine composition is prepared as an injectable, either as a liquid solution or suspension. Injection may be subcutaneous, intramuscular, intravenous, intraperitoneal, intrathecal, intradermal, intraepidermal, or by "gene gun". Other types of administration comprise electroporation, implantation, suppositories, oral ingestion, enteric application, inhalation, aerosolization or nasal spray or drops. Solid forms, suitable for dissolving in or suspension in, liquid vehicles prior to injection may also be prepared. The preparation may also be emulsified or encapsulated in liposomes for enhancing adjuvant effect.

A liquid formulation may include oils, polymers, vitamins, carbohydrates, amino acids, salts, buffers, albumin, surfactants, or bulking agents. Exemplary carbohydrates include sugar or sugar alcohols such as mono-, di-, or polysaccharides, or water-soluble glucans. The saccharides or glucans can include fructose, dextrose, lactose, glucose, mannose, sorbose, xylose, maltose, sucrose, dextran, pullulan, dextrin, alpha- and beta-cyclodextrin, soluble starch, hydroxethyl starch and carboxymethylcellulose, or mixtures thereof "Sugar alcohol" is defined as a C4 to C8 hydrocarbon having an —OH group and includes galactitol, inositol, mannitol, xylitol, sorbitol, glycerol, and arabitol. These sugars or sugar alcohols mentioned above may be used individually or in combination. There is no fixed limit to the amount used as long as the sugar or sugar alcohol is soluble in the aqueous preparation. In some embodiments, the sugar or sugar alcohol concentration is between 1.0% (w/v) and 7.0% (w/v), e.g., between 2.0 and 6.0% (w/v). Exemplary amino acids include levorotary (L) forms of carnitine, arginine, and betaine; however, other amino acids may be added. Exemplary polymers include polyvinylpyrrolidone (PVP) with an average molecular weight between 2,000 and 3,000, or polyethylene glycol (PEG) with an average molecular weight between 3,000 and 5,000. In some embodiments, one can use a buffer in the composition to minimize pH changes in the solution before lyophilization or after reconstitution. Any physiological buffer may be used, but in some cases can be selected form citrate, phosphate, succinate, and glutamate buffers or mixtures thereof. Surfactants that can be added to the formulation are shown in EP patent applications No. EP 0 270 799 and EP 0 268 110.

Additionally, polypeptides can be chemically modified by covalent conjugation to a polymer to increase their circulating half-life, for example. Exemplary polymers, and methods to attach them to peptides, are shown in U.S. Pat. Nos. 4,766,106; 4,179,337; 4,495,285; and 4,609,546. Exemplary polymers are polyoxyethylated polyols and polyethylene glycol (PEG). PEG is soluble in water at room temperature and has the general formula: R(O—CH$_2$—CH$_2$)—O—R where R can be hydrogen, or a protective group such as an alkyl or alkanol group. In some embodiments, the protective group has between 1 and 8 carbons, e.g., methyl. The symbol n is a positive integer, preferably between 1 and 1000, e.g., between 2 and 500. The PEG can have, for example, average molecular weight between 1000 and 40,000, e.g., between 2000 and 20,000, e.g., between 3,000 and 12,000. In some embodiments, PEG has at least one hydroxyl group, e.g., it has a terminal hydroxy group.

Water soluble polyoxyethylated polyols are also useful and can be linked to the CTL polypeptides described herein. They include polyoxyethylated sorbitol, polyoxyethylated glucose, polyoxyethylated glycerol (POG), etc. Another drug delivery system for increasing circulatory half-life is the liposome. The peptides and nucleic acids of the invention may also be administered via liposomes, which serve to target a particular tissue, such as lymphoid tissue, or to target selectively infected cells, as well as to increase the half-life of the peptide and nucleic acids composition. Liposomes include emulsions, foams, micelles, insoluble monolayers, liquid crystals, phospholipid dispersions, lamellar layers and the like. Liposomes either filled or decorated with a desired peptide or nucleic acids of the invention can be directed to the site of lymphoid cells, where the liposomes then deliver the peptide and nucleic acids compositions. Liposomes for use in accordance with the invention are formed from standard vesicle-forming lipids, which generally include neutral and negatively charged phospholipids and a sterol, such as cholesterol. The selection of lipids is generally guided by consideration of, e.g., liposome size, acid lability and stability of the liposomes in the blood stream. A variety of methods are available for preparing liposomes, as described in, e.g., Szoka et al., 1980, and U.S. Pat. Nos. 4,235,871, 4,501,728, 4,837,028, and 5,019,369.

For targeting cells of the immune system, a ligand to be incorporated into the liposome can include, e.g., antibodies or fragments thereof specific for cell surface determinants of the desired immune system cells. A liposome suspension containing a peptide may be administered intravenously, locally, topically, etc., in a dose which varies according to, inter alia, the manner of administration, the peptide being delivered, and the stage of the disease being treated.

After the liquid pharmaceutical composition is prepared, the composition can be lyophilized to prevent degradation and to preserve sterility. Just prior to use, the composition may be reconstituted with a sterile diluent (Ringer's solution, distilled water, or sterile saline, for example) which may include additional ingredients. Upon reconstitution, the composition can be administered to subjects.

The polypeptide and APCs of the invention can be used to treat individuals having gliomas. In some embodiments, the gliomas are selected from glioblastoma (GBM) and diffuse intrinsic pontine gliomas (DIPG). In some embodiments, the individual is a HLA-A2+ type. The HLA genes are the human versions of the major histocompatibility complex (MEW) genes that are found in most vertebrates (and thus are the most studied of the MEW genes). HLAs corresponding to MEW class I are HLA-A, HLA-B, and HLA-C. HLAs corresponding to MHC class II are DP, DM, DOA, DOB, DQ, and DR. Tests for HLA typing are readily available and can be used to screen patients who are likely benefit from the treatment of the invention, for example, from the world wide web at labtestsonline.org/understanding/analytes/hla-testing/tab/test/. In some cases, the patient may also have clinical symptoms besides gliomas. The glioma patient may belong to any age group, including children (e.g., 0-18 years old).

Antibodies Recognizing the CTL Peptides

Also provided is an antibody or an antigen-binding fragment thereof, that recognizes the CTL peptides described herein. Antigen-binding fragments of antibodies encompass fragments which comprise the hypervariable domains designated CDRs (Complementarity Determining Regions) or part(s) thereof encompassing the recognition site for the antigen, i.e., the CTL peptides described herein, thereby defining antigen recognition specificity. Each Light and Heavy chain (respectively VL and VH) of a four-chain immunoglobulin has three CDRs, designated VL-CDR1, VL-CDR2, VL-CDR3 and VH-CDR1, VH-CDR2, VH-CDR3, respectively. Thus, in some cases the antibody comprises fragments of antibodies of the invention (antigen-binding fragments), which comprise or consist of all or a selection of CDRs among VL-CDR1, VL-CDR2, VL-CDR3 and VH-CDR1, VH-CDR2 and VH-CDR3 or functional portions thereof, i.e. portions that exhibit the desired binding specificity, preferably with a high affinity, for the CTL peptides of the invention. For example, in some embodiments, the antibody or antibody fragment binds to SEQ ID NO:2 but does not bind to (e.g., binds at no higher than background) SEQ ID NO:3.

The antibody may be produced by any well-known method for antibody production. For example, the antibody may be obtained by administration of any of the above embodiments of CTL peptides into an animal and harvesting the antibodies produced as a result.

EXAMPLES

Example 1

The H3.3.K27M-derived HLA-A*0201-restricted Cytotoxic T-lymphocyte (CTL) Epitope and Cloning of T-cell Receptor (TCR) cDNAs 1. Screening of HLA-A*0201-binding Epitopes in H3.3 with the K27M Mutation Using the NetMHC 3.4 server (on the world wide web at cbs.dtu.dk/services/NetMHC/), an artificial neural network-based prediction system of peptide binding motifs to HLAs, we predicted that an H3.3-derived 10-mer amino acid (AA) peptide which encompasses the AA position 26-35 including the K27M mutation [H3.3.K27M (26-35)] will serve as a potent epitope in the context of HLA-A*0201, while the non-mutant counterpart for the corresponding positions [H3.3.Non-M (26-35)] was not predicted to have high affinity to HLA-A*0201 (Table 1).

TABLE 1

The H3.3 (26-35) peptide Binding Scores

|  |  | logscore | affinity (nM) |
|---|---|---|---|
| K27M Mutant: | RMSAPSTGGV | 0.477 | 285 |
| Non-mutant: | RKSAPSTGGV | 0.073 | 22651 |

Analysis of H3.3.K27M (26-35), H3.3.Non-M (26-35) peptides as well as 9-mer peptides H3.3.K27M (19-27) and H3.3.Non-M (19-27). We next directly evaluated relative binding affinity of these peptides using the transporter associated with antigen processing (TAP)-deficient HLA- A*0201+ T2 cell line. Since stable binding of HLA-A*0201 with peptide epitopes further stabilizes the surface expression of HLA-A*0201, quantitative expression levels of HLA-A*0201 correlate with the binding affinity of the peptide-epitopes that are co-incubated with the T2 cells (FIG. 1). The MFI values for T2 cells with no peptide indicate the baseline HLA-A2 expression level. Cap6D is a well-documented HLA-A*0201-binding epitope and used as a positive control for the assay. The H3.3.K27M (26-35), but none of other H3.3-derived peptides, demonstrated a peptide-dose-dependent increase of mean fluorescence intensity (MFI). These data suggested that H3.3.K27M (26-35) peptide is a potential epitope for specific T-cell responses. To precisely measure the binding of peptides to HLA-A*02:01 class I molecules, we performed a competitive binding inhibition assay, and evaluated the concentration of peptide yielding 50% inhibition of the binding of the radiolabeled probe peptide (IC50). The mutant H3.3.K27M peptide constantly demonstrated IC50 of 95 nM-187 nM in 4 separate samples, which are considered to be excellent binding capabilities. On the other hand, the non-mutant H3.3 peptide (on the corresponding position) demonstrated >30 fold lower binding capabilities. These data confirm the high HLA A*02:01-binding capability of the H3.3.K27M peptide.

Figure 2A:
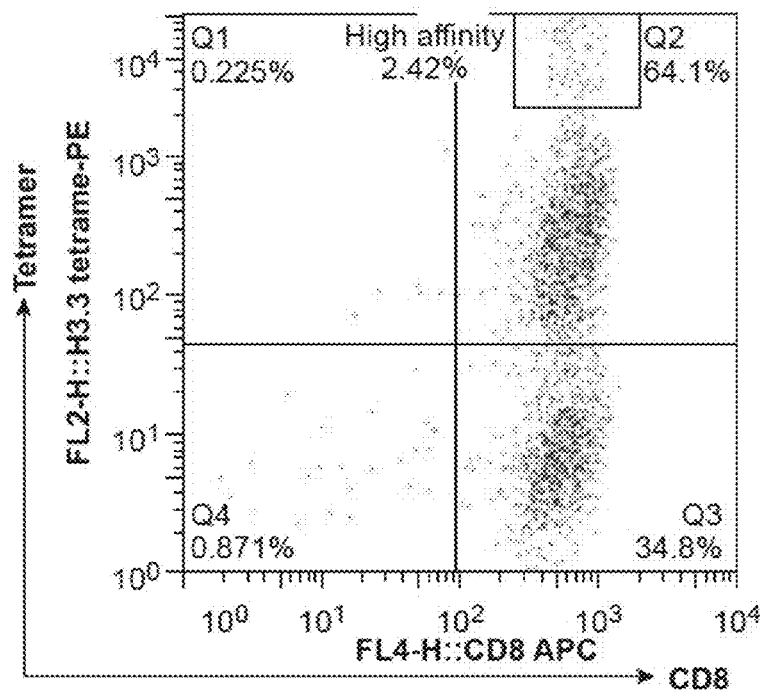
FIGS. 2A-C. HLA-A*0201+ donor-derived CTLs specifically recognize HLA-A*0201+K27M+ glioma cells in an HLA-class I-dependent manner. Peripheral blood mononuclear cells from an HLA-A*0201+ donor were stimulated in vitro with the H3.3.K27M peptide and evaluated for their reactivity against: (1A) HLA-A*0201/H3.3.K27M-specific tetramer and anti-CD8 mAb, and (1B) T2 cells pulsed with the mutant or non-mutated H3.3 peptide by IFN-γ ELISA. In (2A), among the CD8+tetramer+population (64.1% of total lymphocyte-gated cells), there is a tetramer$^{high}$ subpopulation (2.4% of total lymphocyte-gated cells), some of which were used as CTL clones. In (2B), the Cap1-6D peptide (tested at 5 μg/ml only) is a high avidity HLA-A*0201-binding epitope derived from CEA4 used as an irrelevant negative control. (1C) The CTL line was evaluated for cytotoxicity against glioma cell lines T98 (HLA-A*0201+ but K27M-negative), HSJD-DIPG-07 (HLA-A*0201-negative but K27M+), and HSJD-DIPG-13 (HLA-A*0201+ and K27M+) lines. CFSE-labeled target cells (10e4/well) were incubated with CTLs at the E/T ratio of 25 for 4 hours. To block the CTL cytotoxicity, anti-HLA-ABC 10 μg/ml was added to one group. At the end of incubation, 7-ADD was added into each well and incubated for 10 minutes on ice. The samples were analyzed by flow cytometry, and the killed target cells were identified as CFSE+ and 7-ADD+ cells. The cytotoxicity was calculated as the percentage of CFSE+ and 7-ADD+ cells in total HLA-A*0201+ CFSE+ cells. (*p<0.05 by Wilcoxon rank-sum tests).

Then, we stimulated HLA-A*0201 donor-derived peripheral blood mononuclear cells (PBMCs) with synthetic peptide for H3.3.K27M (26-35) in vitro for several weekly cycles and evaluated for the induction of CD8+ T-cells capable of binding the HLA-A*0201-H3.3.K27M (26-35) tetramer, and found over 60% of CD8+ cells bound to the tetramer (FIG. 2A). Furthermore, a subpopulation of the total CD8+ cells in the culture showed distinctively higher levels of binding to the tetramer, suggesting that these are high-affinity binders among the H3.3.K27M (26-35)-reactive T-cell populations.

2. Antigen-specific IFN-γ Production and Lytic Activity of H3.3.K27M (26-35)-stimulated CD8+ T-cells.

Figure 2B:
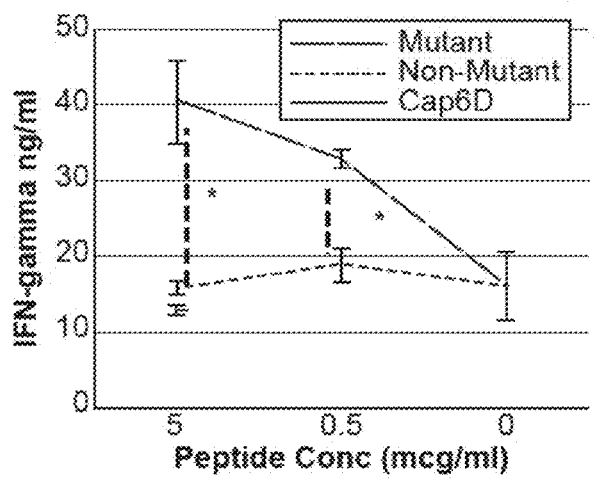
Figure 3:
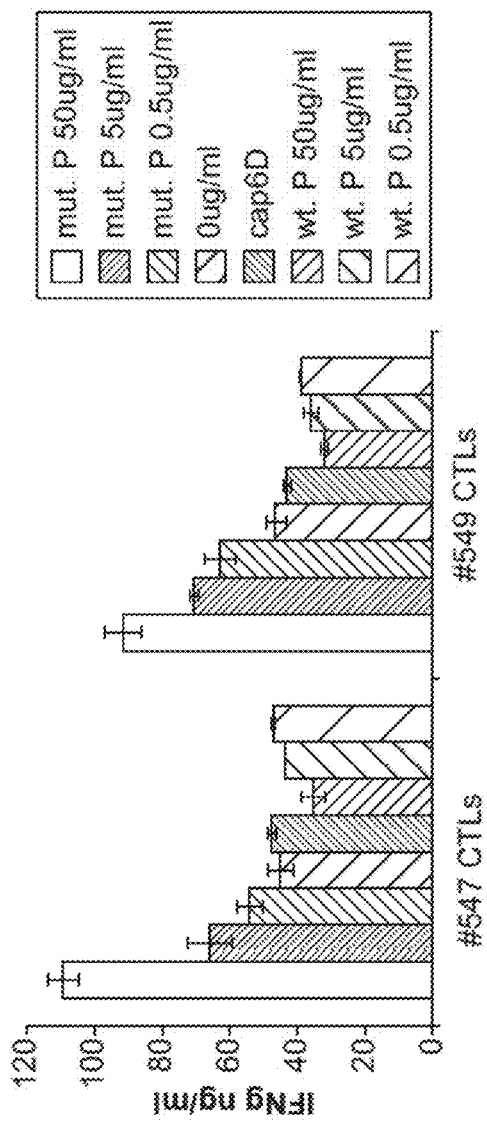
FIG. 3. CD8+ T cell lines stimulated with the H3.3.K27M (26-35) peptide recognize the H3.3.K27M (26-35) but not the non-mutant counterpart. CD8+ T cell lines were induced and expanded with the H3.3.K27M (26-35) peptide from the PBMCs derived from two HLA-A*0201+ healthy donors (#547 and #549). T2 cells pulsed with the mutant H3.3.K27M (26-35) peptide or the non-mutant H3.3.non-M (26-35) peptide at the indicated concentrations were mixed with the CD8+ T cell lines for 24 hours. IFN-γ in the supernatants were assessed by ELISA.

CD8+ T cell lines that had been stimulated with the H3.3.K27M (26-35) peptide demonstrate peptide-dose-dependent increases of IFN-γ production in response to T2 target cells loaded with H3.3.K27M (26-35) compared to T2 cells loaded with the control H3.3.Non-M (26-35), cap6D peptide or nothing (FIGS. 2B and 3).

3. H3.3.K27M (26-35)-stimulated CD8+ T-cells Recognize the Cognate Epitope Endogenously Expressed in HLA-A*0201 Glioma Cells.

Figure 2C:
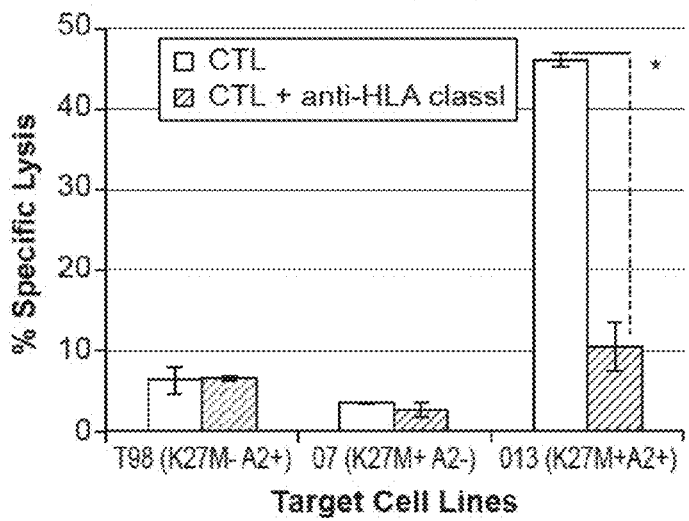
Figure 4:
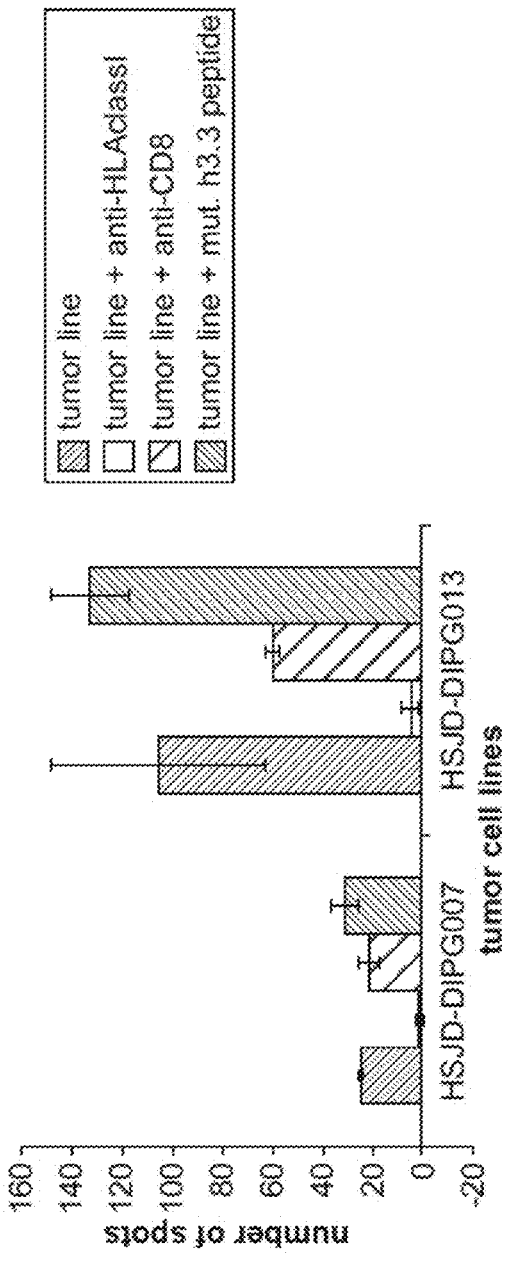
FIG. 4. HLA-A2+ donor-derived CTLs specifically recognize HLA-A2+ K27M+ glioma cells and secrete IFN-γ in an HLA-A2- and CD8-dependent manners. Peripheral blood mononuclear cells from an HLA-A2 donor were stimulated in vitro with synthetic peptides for H3.3.K27M (26-35) and evaluated their reactivity against HSID-007 (HLA-A2-negative but K27M+) or HSID-013 (HLA-A2+ and K27M+) lines by IFN-γ ELISPOT assays. Anti-HLA-ABC (10 μg/ml) and anti-CD8 antibodies were also used to evaluate whether the response is dependent on HLA-A2 and CD8+, respectively.

We next examined whether the CD8+ T-cell line developed in response to the H3.3.K27M (26-35) peptide recognize HLA-A*0201+ human glioma cells that endogenously express and present the H3.3.K27M (26-35) epitope. We used HSID-007 (HLA-A*0201-negative but K27M+) or HSID-013 (HLA-A*0201+ and K27M+) as target glioma cells. As illustrated in FIG. 2C and FIG. 4, the CD8+ T-cell line responded to HSID-013 but not to HSID-007 cells based on cytotoxic T-lymphocyte (CTL) assays (FIG. 2C). Furthermore, the observed response against HSID-013 cells was almost completely blocked by anti-HLA-class I blocking antibody. These data are notable because they indicate that the CD8+ T-cell lines (we have similar data for two additional cell lines; but only one is shown here) recognize the H3.3.K27M (26-25) mutant epitope endogenously expressed and presented by HLA-A*0201+ glioma cell lines.

4. High Affinity H3.3.K27M-specific CTL Clones.

Figure 5A:
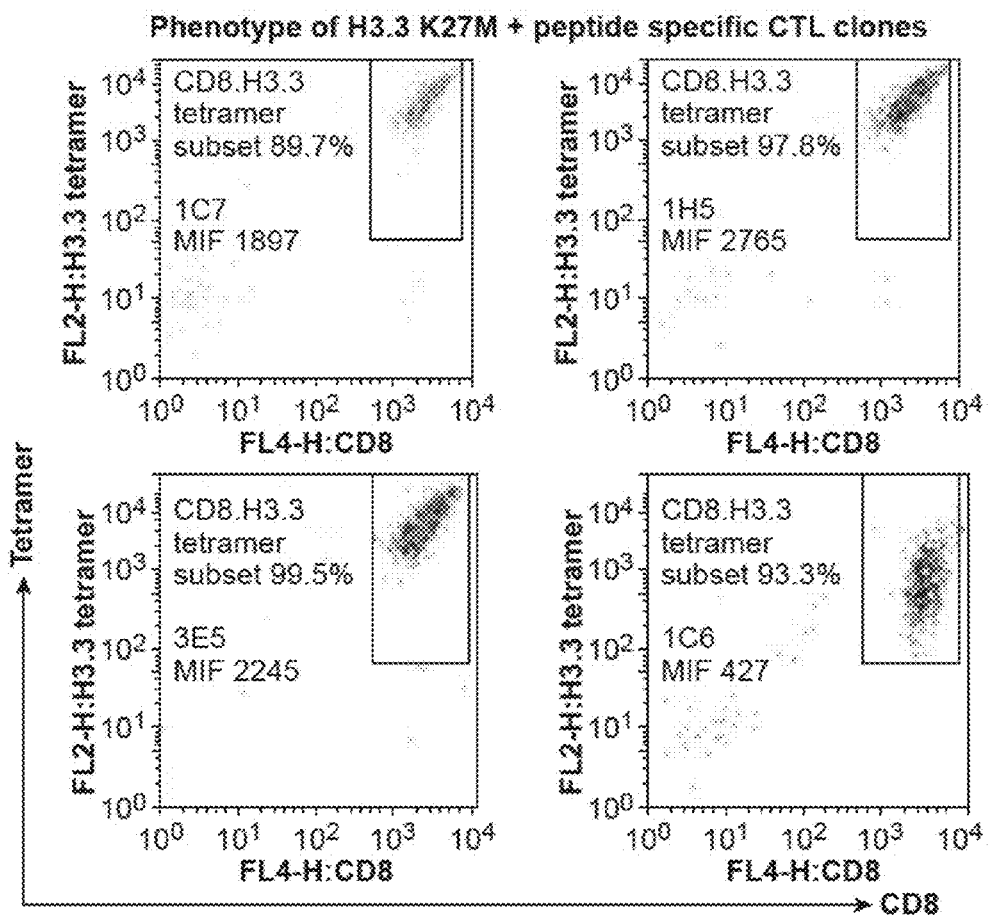
FIG. 5A-B. Characterization of H3.3.K27M-specific CTL clones. (5A) Clones were generated by limiting dilution cloning of HLA-A2-H3.3.K27M-tetramer-positive single cells from H3.3 K27M-specific CTLs using FACS-sorting. Clones with relatively high (1C7, IH5 and 3E5) and moderate (1C6) affinity based on the mean fluorescence index (MFI) were selected for further evaluations. (5B) An H3.3.K27M-specific CTL clone (IH5) demonstrates H3.3.K27M-specific reactivity as shown by IFN-γ ELISA against T2 cells pulsed with the mutant H3.3 K27M+ peptide at titrating concentrations and the wild-type peptide (H3.3 K27M-negative; used at 500 ng/ml).
Figure 5B:
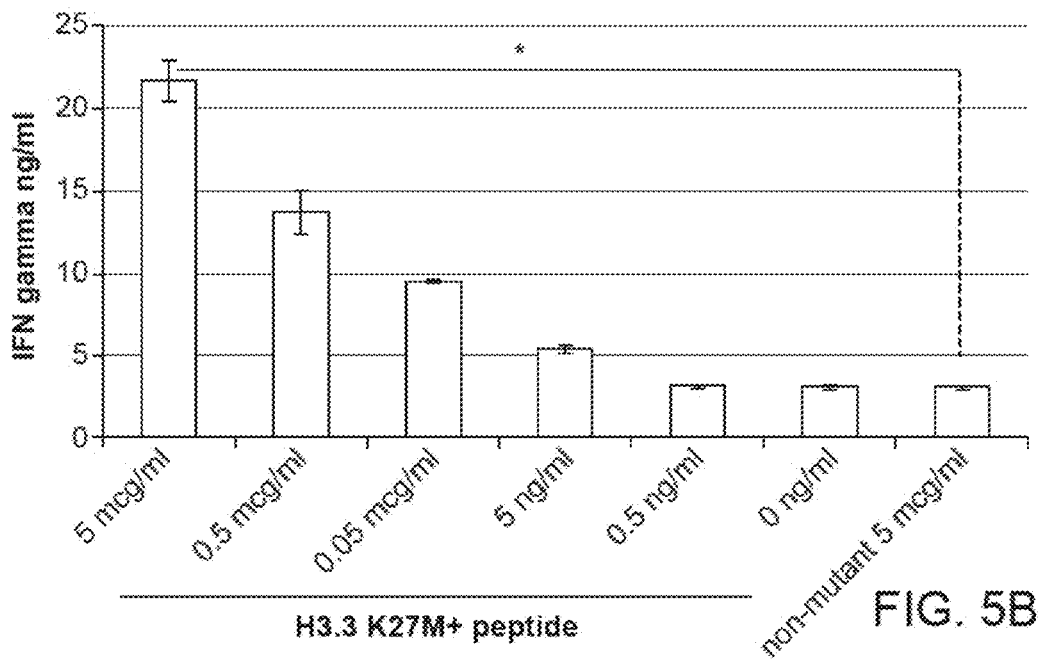

We have obtained CTL clones that are reactive to the H3.3.K27M epitope (FIG. 5A-B). These clones retain specificity to the H3.3. K27M epitope and we have isolated T-cell receptor (TCR) α and β chains from the clone 1H5.

5. Cloning of H3.3.K27M-specific T-cell Receptor cDNA.

Figure 6A:
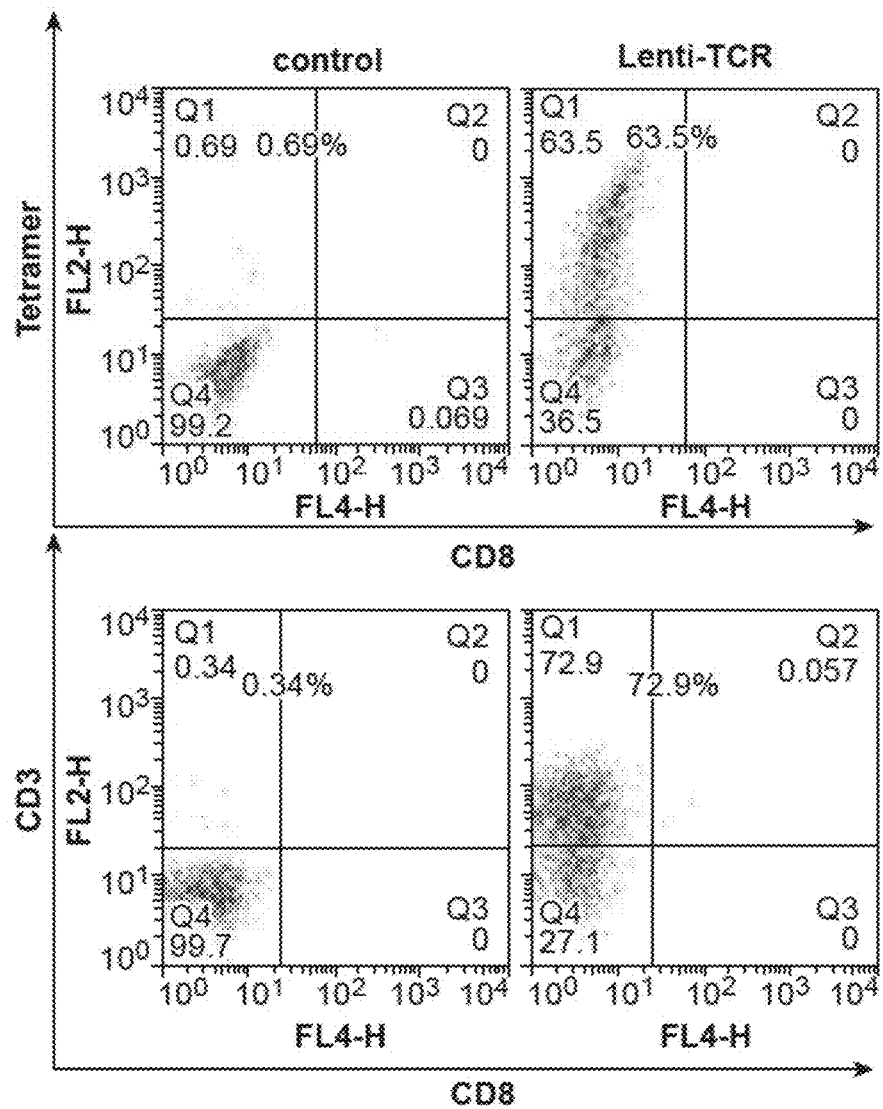

We have cloned full-length α- (SEQ ID NO:8) and β-chains (SEQ ID NO:10) of TCRs from an H3.3.K27M-specific CD8+ T-cell clone (1H5), and constructed a lentiviral vector encoding the α- and β-chains. As the first step to confirm expression of the transgene-TCR, we transduced J.RT3-T3.5 cells, which are deficient for endogenous TCR β-chain, with the lentiviral vector and evaluated for expression of HLA-A*0201/H3.3.K27M-tetramer-reactive TCR by flow cytometry (FIG. 6A; upper panels; FIG. 7). More than 60% of J.RT3-T3.5 cells showed positive tetramer binding, whereas only 0.69% of non-transduced J.RT3-T3.5 cells showed the signal, indicating that the transgene TCR is expressed by both lentiviral constructs. In the same setting, we also observed that TCR-transduced cells, but not control cells upregulate CD3 expression when co-incubated with the tetramer (FIG. 6A lower panels). These cells also upregulate CD69 as an indication of activation in a peptide-dose-dependent, and TCR-specific manner (FIG. 6B). These data clearly indicate antigen-specific reactivity of the TCR when transduced in J.RT3-T3.5 cells.

Finally, TCR-transduced cells, but not control cells, were able to produce IL-2 when they were co-cultured with HLA-A*0201+, H3.3.K27M+ DIPG-013 cells (FIG. 6C).

6. Absence of Detectable Deiminated H3 Protein in Cultured Glioma Cells

The natural process of deimination can convert histone arginine to citrulline, including the arginine residue within the H3.3.K27M epitope. Therefore, it is useful to determine whether glioma cells undergo deimination, and, if so, whether the replacement of the arginine residue within the H3.3.K27M epitope with citrulline (i.e. deimination) impacts the immunogenicity of the H3.3.K27M epitope.

We performed Western blot analyses to determine whether H3.3.K27M+ glioma cells have deiminated H3 protein using a mAb specific to deiminated H3 (abcam cat# ab19847). While neutrophils stimulated with calcium ionophore as the positive control sample showed a single band of approximately 15 kDa corresponding to the deiminated H3, none of the glioma cell lines demonstrated a similar band, strongly suggesting that glioma cell lines are not substantially deiminated, at least when cultured in vitro. The positive control sample is from neutrophils stimulated with calcium ionophore. Glioma cells evaluated are HSJD-DIPG-13, HSJD-DIPG-12, HSJD-DIPG-08, HSJD-DIPG-07, SU06, SU-D-04, T98, and U87. Each lane was loaded with 20 µg protein lysate and high quality SDS-PAGE was confirmed each time by Coomassie Blue staining. We repeated these Western blot analyses at least 4 times (4 SDS-PAGE runs) with different incubation and exposure conditions, and found a thin band with glioma cells at very high exposure conditions (not shown), suggesting that deimination may occur in cultured glioma cells at low levels.

7. Alanine Scanning Data Suggests that there are No Known Human Proteins that Share the Key Immunogenic AA Residues of the H3.3.K27M Epitope To ensure the specificity and safety of the H3.3.K27M-targeting approach, it is useful to determine key AA residues in the H3.3.K27M epitope that are responsible for the CTL reactivity. This will allow precise predictions and assessments for cross-reactivity to other epitopes derived from proteins in non-tumor normal cells.

Figure 8A:
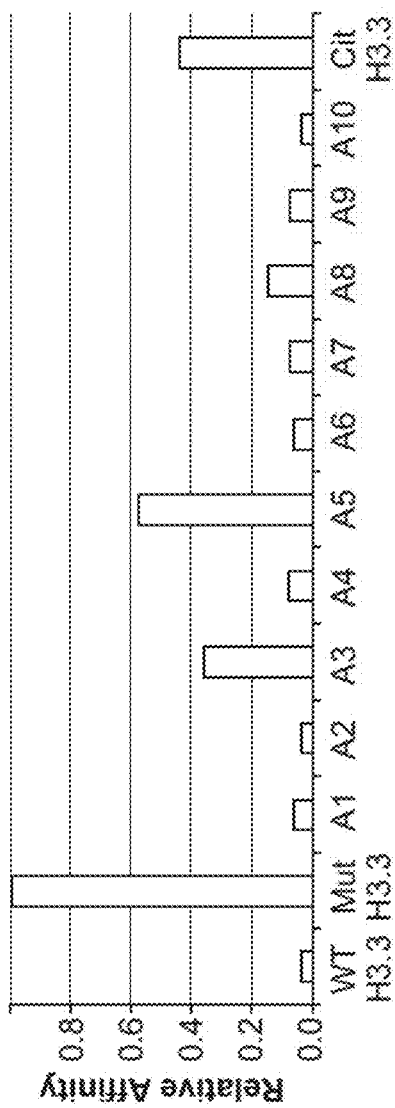
FIG. 8A-B. Alanine scanning to determine the key immunogenic AA residues of the H3.3.K27M epitope. (8A) Relative HLA-A2-binding affinity of each peptide to that of H3.3.K27M (26-35) was determined by cell-free binding assay using HLA-A2 purified by affinity chromatography from the EBV transformed homozygous cell line JY. (8B), J.RT3-T3.5 cells were transduced with lentiviral vector encoding the H3.3.K27M-specific TCR and evaluated for the recognition of each peptide loaded on T2 cells by production of IL-2. Each group was assayed as triplicate *<0.05 by Student-t compared with the mutant H3.3. In addition to 10 synthetic peptides each containing the substitution with alanine (A1-A10), we also evaluated synthetic peptides designed for citrullinated H3.3. K27M epitope (Cit H3.3; i.e., the first AA of the H3.3.K27M epitope is replaced by citrulline) and H3.1 (a homologue of H3.3.) derived K27M epitope (Mut H3.1).
Figure 8B:
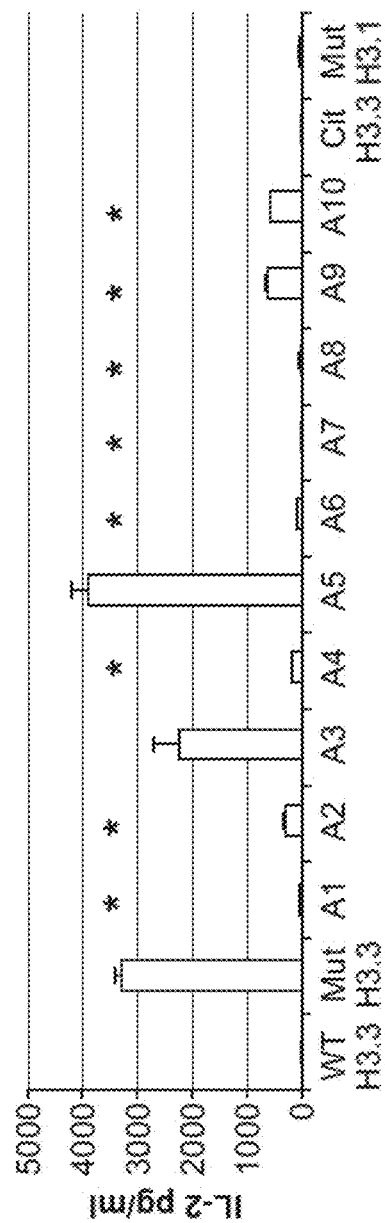

To this end, alanine-scanning mutagenesis was used. Single alanine mutations (10 in total) were introduced at every AA residue within the H3.3.K27M decamer (10-mer)

epitope. Hence, 10 synthetic peptides each containing the specific substitution with alanine were prepared (A1-A10). Using each of the synthetic peptides with alanine-substitutions, we evaluated whether the substitution alters the stability of peptide-binding to HLA-A*0201 (FIG. 8A). When the binding is diminished by the substitution compared with the natural H3.3.K27M epitope ("Mut H3.3." in FIG. 8A-B), it indicates that the substituted residue was critical for HLA-A*0201-binding. We also evaluated whether the H3.3.K27M-specific TCR recognizes the altered epitopes presented on T2 cells. To this end, we evaluated IL-2 production as the readout for the activation of TCR-transduced J.RT3-T3.5 cells when co-cultured with T2 cells loaded with each of the altered peptides (FIG. 8B). AA substitutions that diminish IL-2 production (which was seen with the Mut H3.3 peptide) tell us critical AA for recognition by the TCR. Both binding—(FIG. 8A) and function (i.e., IL-2)—(FIG. 8B) based approaches consistently showed that AA at positions 1, 2, 4, 6, 7, 8, 9 and 10 are critical for the recognition. We then carried out an in silico search to identify naturally existing AA sequences using NCBI BLAST. We found no known human proteins that contain the same AA residues, indicating that it would be highly unlikely that immunotherapy targeting this epitope will cause unwanted off-target reactions against normal cells.

We also evaluated whether the H3.3.K27M-specific TCR is reactive to the deiminated H3.3K.27M epitope using a synthetic peptide in which the arginine residue of the H3.3.K27M epitope is replaced by citrulline (Cit H3.3) (FIG. 8A-B). While the Cit H3.3 peptide partially retains its affinity to HLA-A*0201 (FIG. 8A), it completely abrogates IL-2 production by TCR-transduced J.RT3-T3.5 cells, indicating that the TCR does not recognize the Cit H3.3 peptide.

A subpopulation of glioma patients bears the K27M mutation in H3.1 (a homologue of H3.3). The AA sequences encompassing the K27M mutation in H3.1 and H3.3 are similar. When compared with the H3.3.K27M epitope, the corresponding portion of H.3.1 has only one AA substitution. Hence, we evaluated whether the TCR against the H3.3 K27M cross-reacts against H3.1 K27M using a synthetic peptide designed for the putative H3.1 K27M epitope (Mut H3.1 in FIG. 8B). The TCR failed to recognize the Mut H.3.1 epitope, suggesting that patients with the H3.1.K27M mutation but without H3.3.K27M mutation are not eligible for prospective TCR-transduced adoptive transfer therapy.

Example 2

Figure 9A:
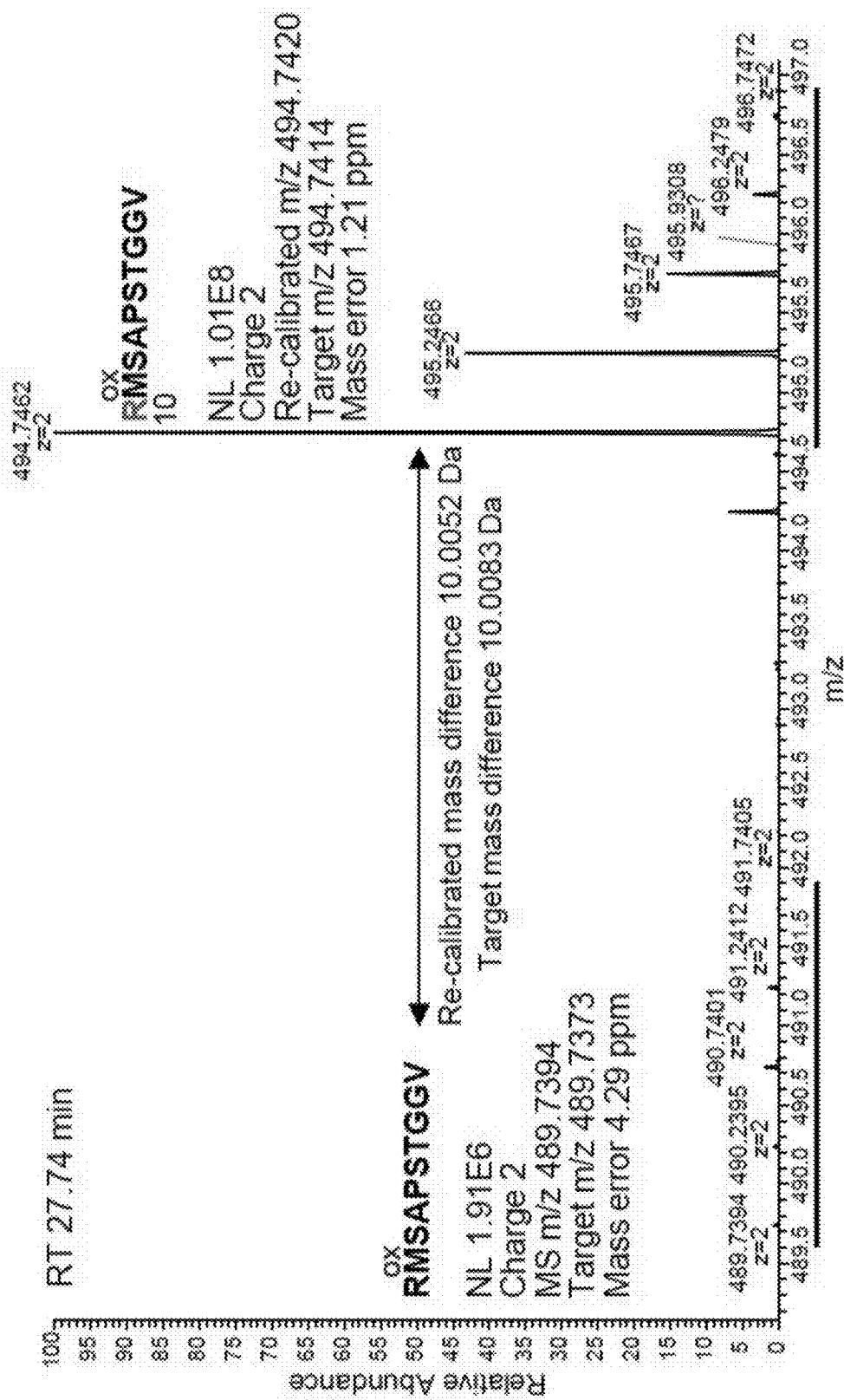
FIG. 9A-C. The H3.3K27M peptide is detectable by LC-MS/MS in the HLA-class I immunopeptidome of glioma cells bearing the H3.3K27M mutation. HLA-class I peptides were biochemically purified from U87H3.3K27M glioma cells and analyzed by LC-MS/MS with a synthetic heavy version of the H3.3K27M peptide as the reference. 9A. U87H3.3K27M HLA-class I immunopeptidome (SEQ ID NO:2) shows two co-eluting isotope patterns corresponding to the target m/z and mass difference of the oxidized forms of the heavy and the endogenous H3.3K27M peptides. 9B. Fragmentation spectrum of the heavy peak, showing identification of the oxidized heavy H3.3K27M peptide. 9C. Zoom-in of the light isotope pattern shows m/z values and distances between peaks as expected from the endogenous H3.3K27M peptide.
Figure 9B:
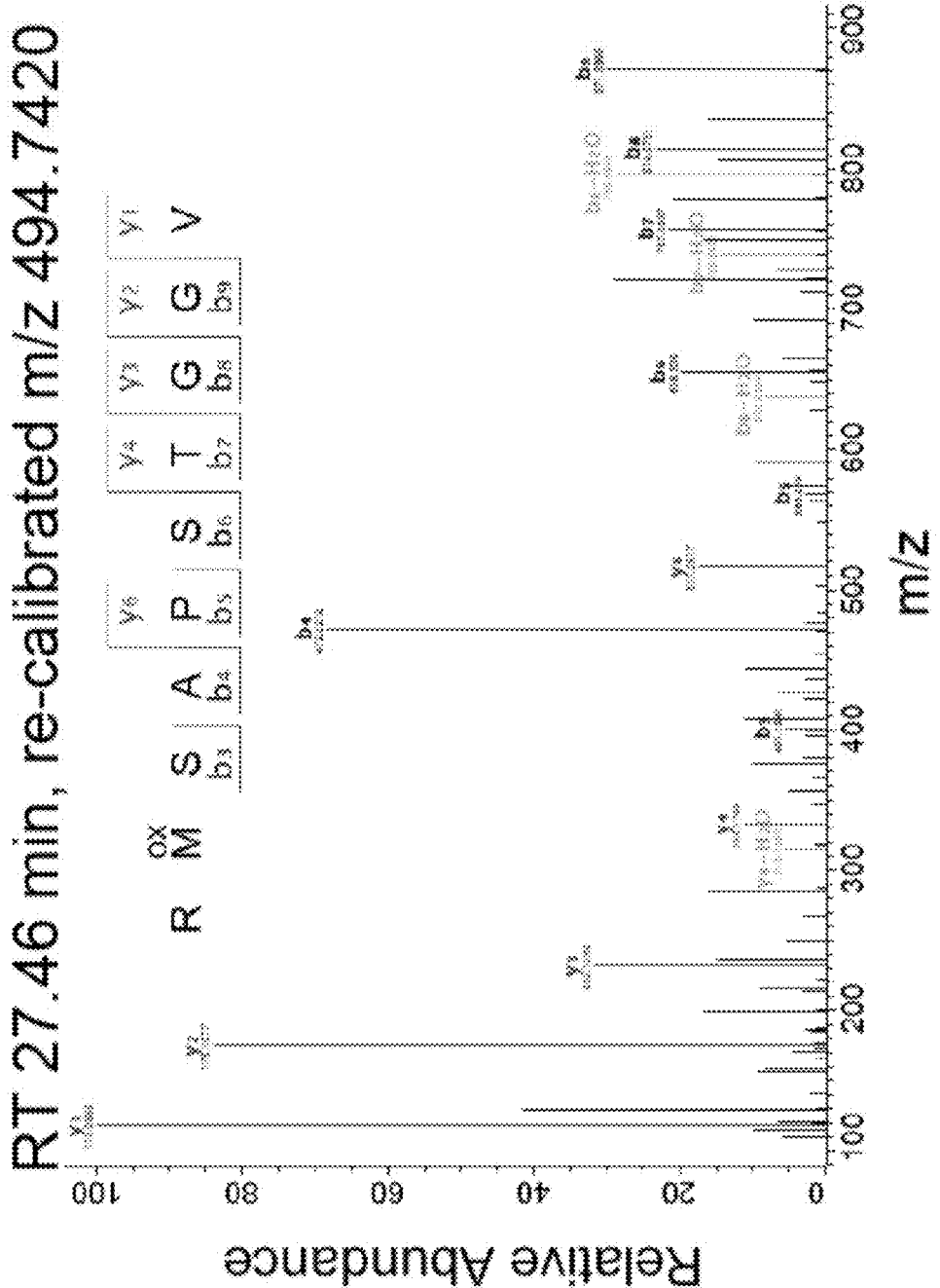
Figure 9C:
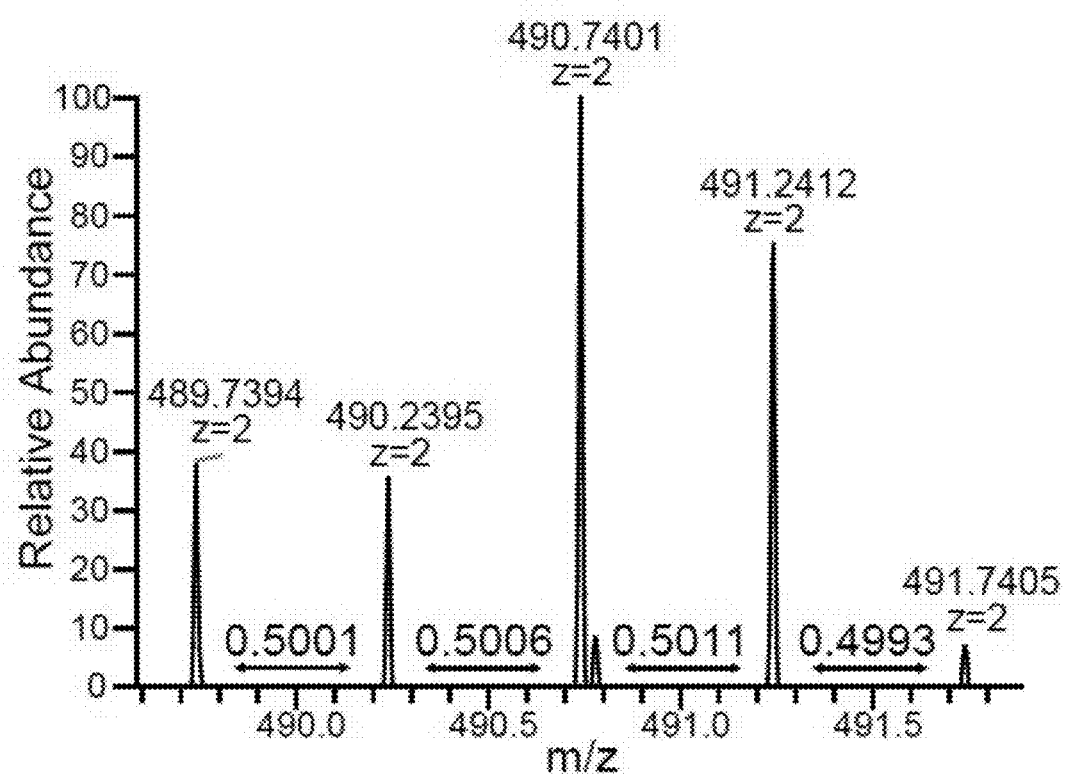

The H3.3K27M Peptide is Presented as an HLA-A*02:01+-Binding Epitope by Glioma Cells Harboring the H3.3K27M Mutation To investigate whether the bioinformatically predicted H3.3K27M$_{26-35}$ peptide is produced and presented by the HLA machinery in HLA-A*02:01$^+$H3.3K27M$^+$ glioma cells, we used a recently developed mass spectrometry (MS)-based method for the direct identification of HLA-class I-binding peptides (17). We purified HLA-class I-binding peptides from HLA-A*02:01$^+$U87MG glioma cells stably transduced with cDNA encoding H3.3K27M (U87H3.3K27M) or H3.3WT (U87H3.3WT), or parental U87MG cells, and analyzed them by LC-MS/MS using a Quadrupole Orbitrap Mass Spectrometer. To specifically identify the H3.3K27M$_{26-35}$ peptide, we added a fixed amount of a synthetic version of the H3.3K27M$_{26-35}$ 10-mer to each sample containing a substitution of arginine at position 1 with the heavy counterpart ($^{13}$C6 $^{15}$N4 arginine), thus introducing a 10.0083 Da mass difference. With this approach, the heavy labeled peptide was readily sequenced and identified because of its higher abundance during LC-MS/MS analysis. Since both the heavy and light peptides elute at the same time from the chromatographic column and differ exclusively in the introduced mass change, it was possible to confidently identify the endogenous peptide even at extremely low concentrations and in the absence of an MS/MS spectrum. Following re-calibration in MaxQuant, we detected two co-eluting isotope patterns with mass to charge (m/z) ratios of 494.7420 and 489.7394 at 27.74 minutes of chromatographic separation in U87H3.3K27M glioma cells (FIG. 9A). This was compatible with the predicted values for both the heavy and the endogenous H3.3K27M$_{26-35}$ peptides in their oxidized forms (494.7414 and 489.7373, respectively) with a relative mass difference of 10.0052 Da. The elution peak corresponding to the heavy peptide was selected multiple times for sequencing and its fragmentation spectrum was unequivocally identified as the oxidized form of the heavy H3.3K27M (Andromeda identification score 124.23; FIG. 9B). The putative light isotope pattern presented correct m/z values for each of its isotopic peaks (FIG. 9C). Moreover, this isotope pattern was detectable exclusively in U87H3.3K27M cells but not in either the parental U87 or the U87H3.3WT cells (data not shown). The modification observed in both peptides is due to the oxidation of the methionine residue during the experimental sample preparation procedure and therefore does not reflect the state of the peptide in vivo (18). Together, these observations demonstrate that the H3.3K27M$_{26-35}$ epitope peptide is naturally produced and presented by HLA class I on the surface of glioma cells bearing the H3.3K27M mutation.

Figure 10A:
FIG. 10A-D. Cloning of cDNA for the H3.3K27M-specific TCR and construction of a retroviral vector for efficient transduction of human T-cells. 10A. Schema of the TCR retroviral vector design. Synthesized TCR cDNA fragments derived from the CD8+ T-cell clone 1H5 were inserted into the Not I/Xho I site of Takara siTCR vector plasmid together with the Kozak sequence, spacer sequence (SP) and P2A sequence. 10B. T2 cells loaded with or without H3.3K27M peptide (10 μg/ml) were co-cultured with either control or TCR-transduced J76CD8+ cells in 1:1 ratio and assessed for IL-2 production by ELISA. Data represent three independent experiments with similar results. *p<0.05 compared with each of other groups. 10C. Human PBMCs were transduced with the retroviral TCR vector and CD3+ T-cells were evaluated for transduction efficiency in CD8+ and CD8− T-cell populations by the specific tetramer. 10D. TCR-transduced or control CD8+ T-cells were co-cultured with T2 cells loaded with H3.3K27M, H3.3WT, or an irrelevant influenza matrix M1$_{58-66}$ peptide in 1:1 ratio for 8 hrs, and evaluated for CD69 expression as an activation marker. Dot plots represent % CD69$^+$ cells among CD8$^+$ T-cells. n=3 in each group. Data represent two independent experiments with similar results. *p<0.05 compared with each of other groups.
Figure 10B:
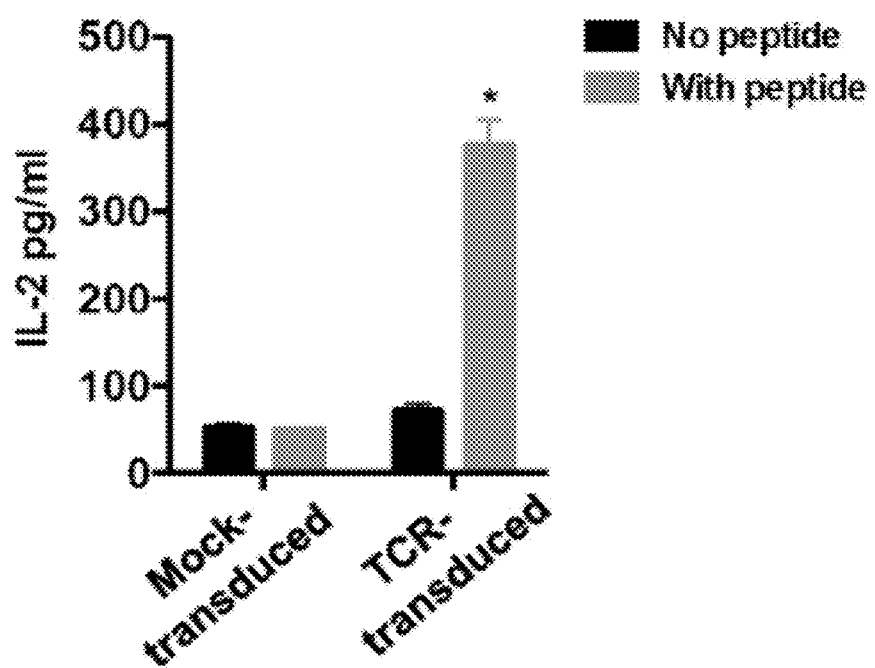
Figure 10C:
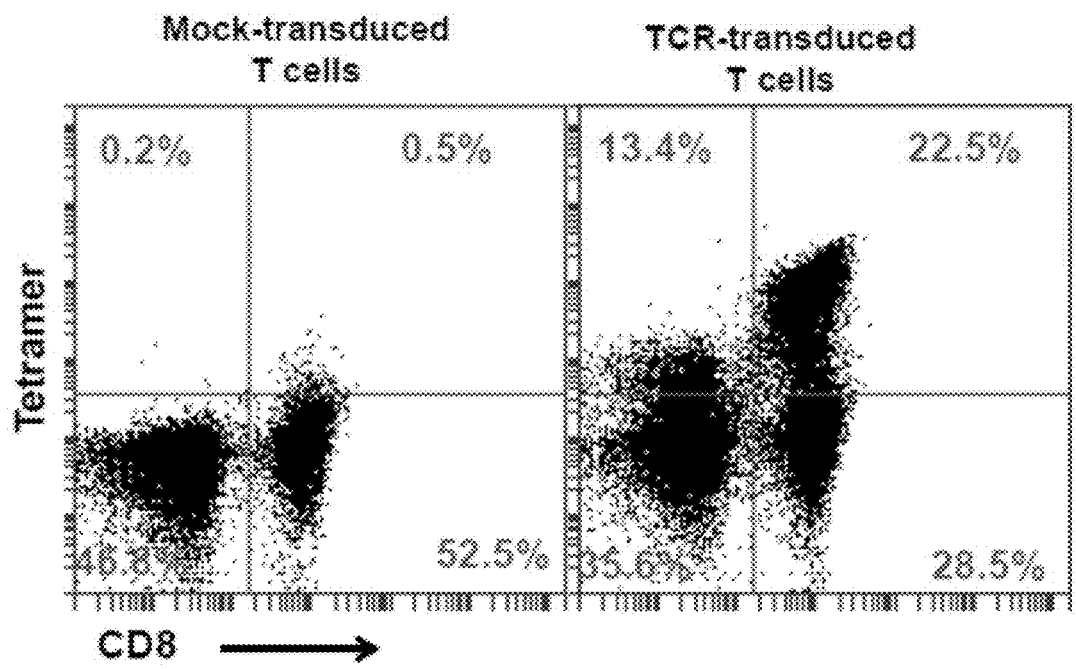
Figure 10D:
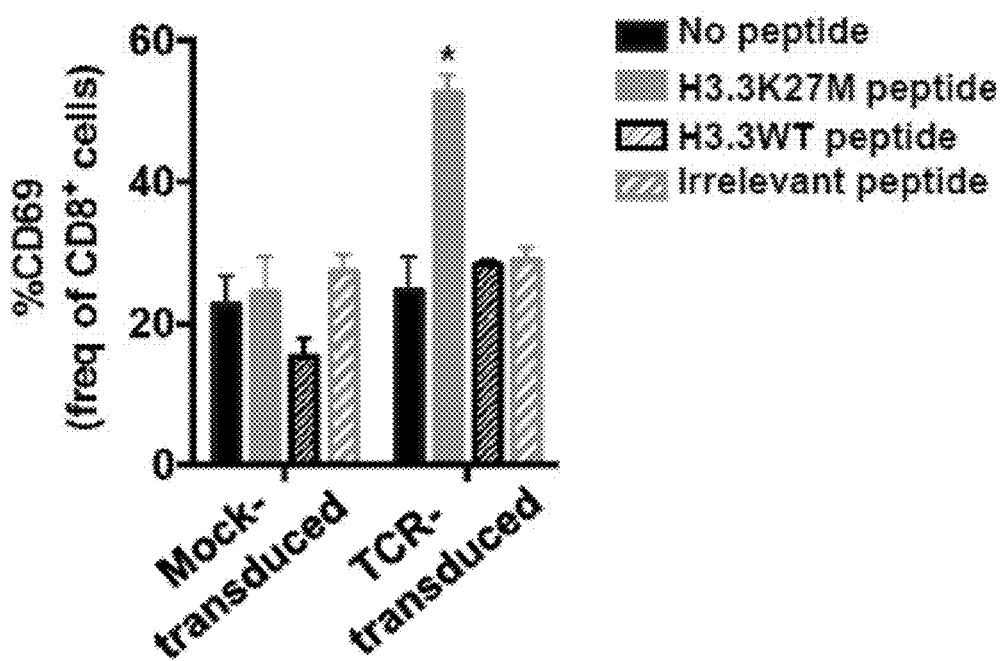

Human T-cells Transduced with Retroviral Vector Encoding H3.3K27M-specific TCR Demonstrate H3.3K27M-specific CTL Reactivity We isolated full-length cDNA for α- and β-chains of TCR from the clone 1H5, optimized the codon usage, and cloned them into a TCR retroviral vector system, which incorporates small interfering RNA (siRNA) targeting constant regions of the endogenous TCR α- and β-chains to avoid mispairing between endogenous and transgene TCR chains (S. Okamoto, Y. Amaishi, Y. Goto, H. Ikeda, H. Fujiwara, K. Kuzushima, M. Yasukawa, H. Shiku, J. Mineno, *Mol Ther Nucleic Acids* 1, e63 (2012); S. Okamoto, J. Mineno, H. Ikeda, H. Fujiwara, M. Yasukawa, H. Shiku, I. Kato, *Cancer Res* 69, 9003-9011 (2009)) (FIG. 10A). To evaluate the function of the transgene TCR, we first transduced the Jurkat T-cell clone 76 (J76CD8) (21), which is deficient in endogenous TCR α- and β-chains but expresses human CD8, with the TCR vector or with a mock vector. This experiment demonstrated that TCR-transduced but not control mock-transduced J76CD8 cells produced elevated levels of IL-2 when stimulated with the H3.3K27M peptide (FIG. 10B). Next, we transduced primary human T-cells with the TCR and achieved over 40% transduction efficiency in CD8$^+$ T-cells and approximately 20% in CD8$^-$ T-cells based on tetramer-staining, suggesting the CD8 co-receptor is important for efficient expression of the TCR (FIG. 10C). We also observed a significant up-regulation of the T-cell activation marker, CD69 (22), on TCR-transduced T-cells but not mock-transduced control T-cells, upon stimulation with the H3.3K27M$_{26-35}$ mutant peptide but not WT or an additional irrelevant, influenza-A-derived HLA-A*0201-binding peptide (FIG. 10D).

Figure 11:
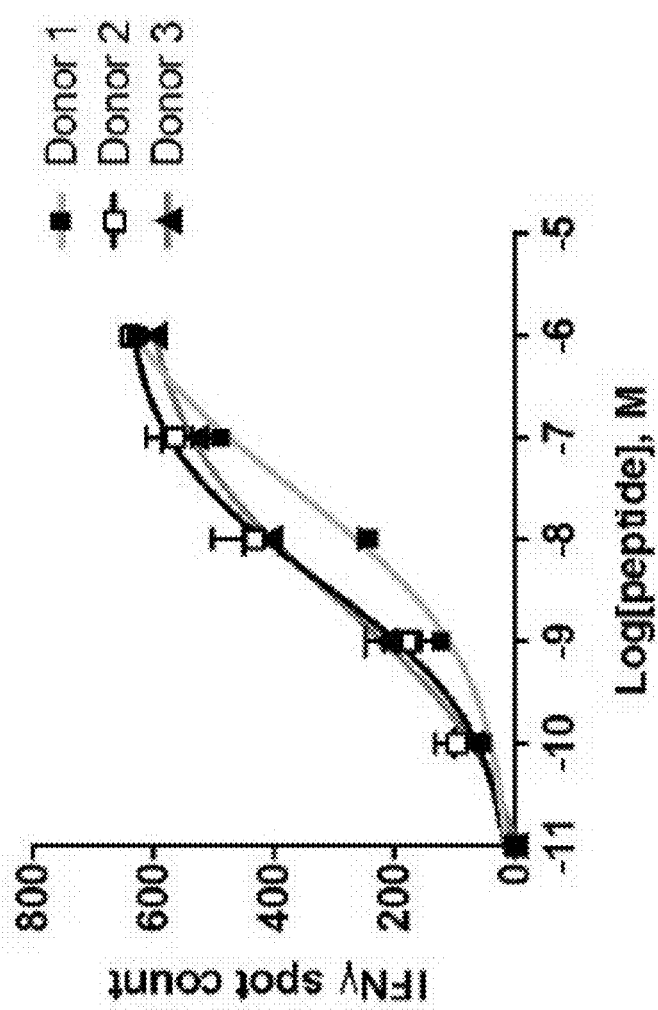
FIG. 11. Evaluation of TCR avidity to the HLA-A2-peptide complex. T2 cells loaded with titrating concentrations of the H3.3K27M peptide (5×10$^3$/well) were co-cultured with TCR-transduced CD8$^+$ T-cells derived from 3 donors (5×10$^3$/well), and then assessed for IFN-γ secretion by ELISPOT. The half-maximal effective concentration (EC$_{50}$) of the peptide was calculated using non-linear regression analysis. Each experiment was carried out in triplicate, and data represent two independent experiments with similar results.

TCR-transduced Primary T-cells Recognize the H3.3K27M Peptide at 10$^{-8}$ to 10$^{-9}$ M To evaluate the functional avidity of the TCR, we determined the peptide concentration required to induce half-maximal response (EC$_{50}$), using IFN-γ production by TCR-transduced T-cells as the readout of response. Using CD8$^+$ T-cells derived from 3 healthy HLA-A*02:01$^+$ donors and co-culturing them with T2 cells loaded with titrating doses of the H3.3K27M peptide, we determined the EC$_{50}$ of TCR-transduced T-cells to be between 10$^{-8}$ to 10$^{-9}$ M based on IFN-γ enzyme-linked immuno-spot (ELISPOT) assay (FIG. 11).

Figure 12A:
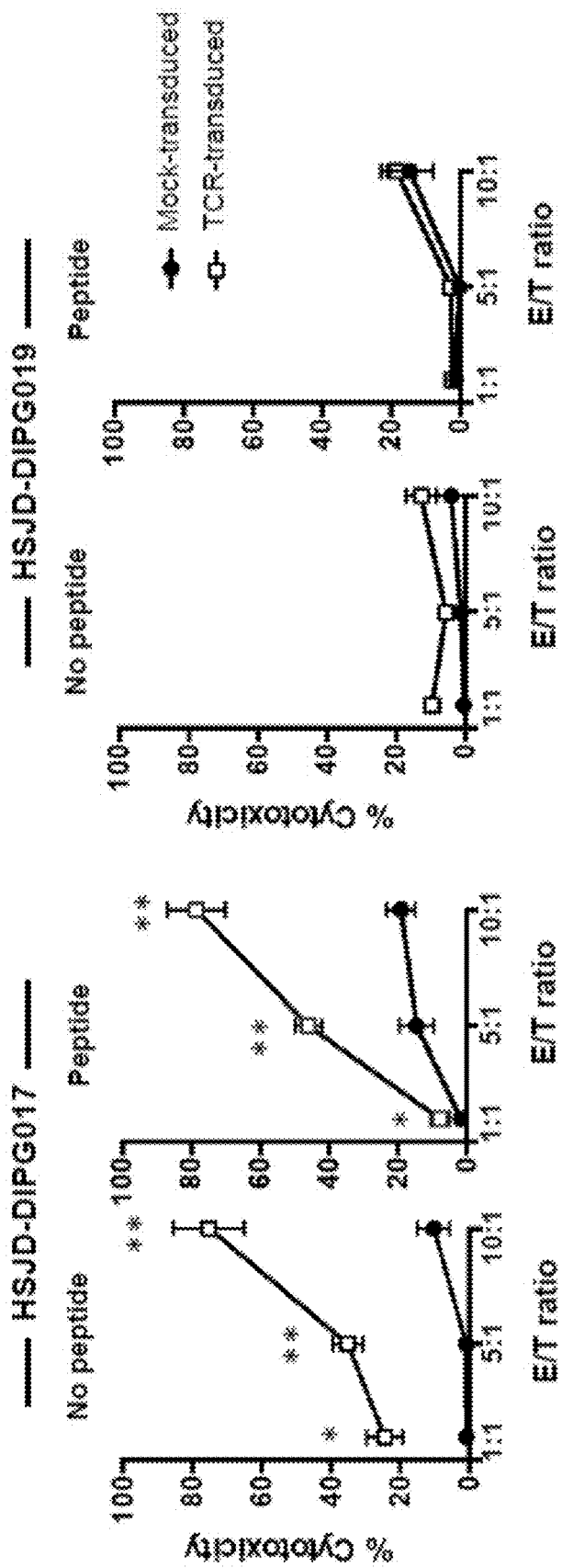
FIG. 12A-C. TCR-transduced T-cells lyse H3.3K27M$^+$ HLA-A2$^+$ glioma cells in an HLA-A*0201- and H3.3K27M-dependent manner. 12A and 12B. Cytotoxicity of TCR-transduced T-cells was evaluated by lactate dehydrogenase (LDH) cytotoxicity assay. Exogenous, synthetic H3.3K27M peptide (10 m/ml) was added as a positive control group for TCR reactivity for each cell line. HLA-A2 blocking antibody was added in one group for each cell line to determine the HLA-A2-dependent TCR reactivity. 12A. TCR-transduced or mock-transduced T-cells were co-cultured with H3.3K27M$^+$HLA-A*0201$^+$ HSJD-DIPG-017 cells or control H3.3K27M$^+$HLA-A*0201$^-$HSJD-DIPG-019 cells at E/T ratio of 1, 5, and 10 for 24 hrs. 12B. TCR-transduced or control T-cells were co-cultured with HLA-A*0201$^+$U87H3.3K27M cells or U87H3.3WT cells at E/T ratio of 5. 12C. CFSE-labeled target cells (U87H3.3K27M and U87H3.3WT cells) were co-cultured with TCR-transduced or control T-cells with or without exogenous peptide at E/T ratio of 5. After 24 hr incubation, cells were stained with 7AAD. % CFSE$^+$7 AAD$^+$ cells indicated specific percent cytotoxicity. Each group was assessed in triplicate. Data represent two independent experiments with similar results. *p<0.05, **p<0.01 based on Student's t test comparing TCR-transduced T-cells with the mock-transduced T-cells.
Figure 12B:
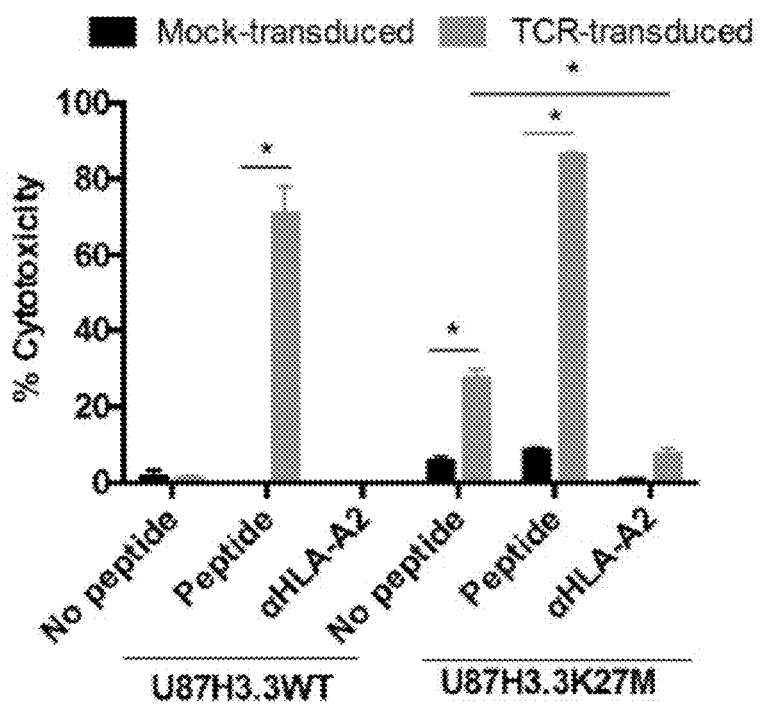
Figure 12C:
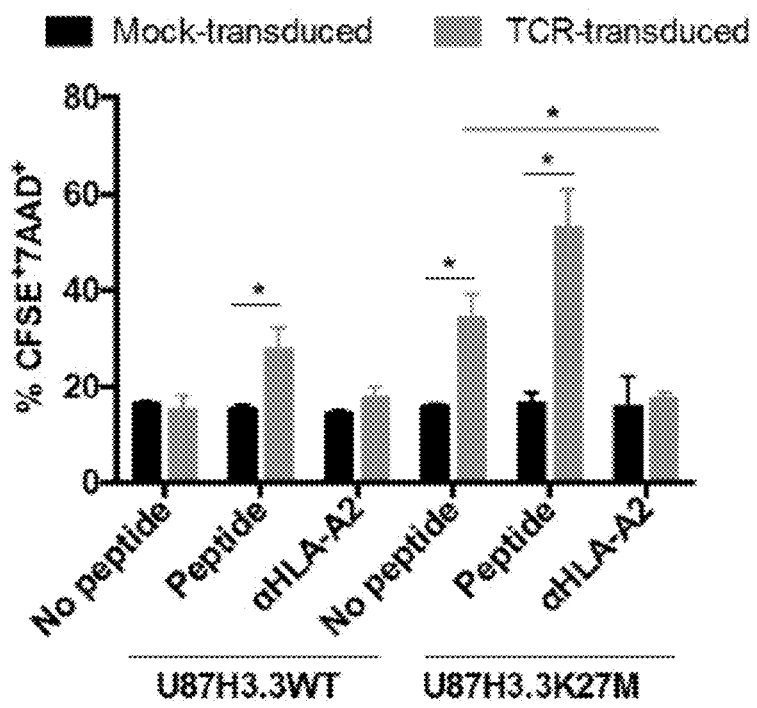

TCR-transduced T-cells Specifically Lyse H3.3K27M$^+$ HLA-A2$^+$ Glioma Cells In Vitro It is essential to demonstrate that TCR-transduced T-cells are able to recognize the H3.3K27M epitope which is endogenously expressed in glioma cells, and lyse H3.3K27M$^+$HLA-A*02:01$^+$ glioma cells. To this end, we evaluated cytotoxicity of TCR-transduced T-cells against H3.3K27M$^+$HLA-A2$^+$HSJD-DIPG-017 cells using lactate dehydrogenase (LDH) detection-based cytotoxicity assay. While both TCR-transduced and control mock-transduced T-cells were similarly activated, only TCR-transduced T-cells lysed HSJD-DIPG-017 cells. Addition of synthetic H3.3K27M peptide further enhanced the lysis by TCR-transduced T-cells (FIG. 12A). Furthermore, the observed lysis was dependent on HLA-A*02:01 as TCR-transduced T-cells were not able to lyse HLA-A*02:01$^{-neg}$ H3.3K27M$^+$ HSJD-DIPG-019 cells, even in the presence of exogenously added H3.3K27M peptide (FIG. 12A). To demonstrate that the reactivity of TCR-transduced T-cells is specific to the H3.3K27M, we used HLA-A*02:01$^+$ U87MG glioma cells stably transduced with cDNA encoding H3.3K27M (U87H3.3K27M) or H3.3WT (U87H3.3WT; FIGS. 12B and C). TCR-transduced T-cells efficiently lysed U87H3.3K27M cells but not U87H3.3WT cells. Lysis of U87H3.3K27M cells was enhanced when synthetic H3.3K27M peptide was added but abrogated by the anti-HLA-A2 blocking antibody. On the other hand, TCR-transduced T-cells lysed U87H3.3WT cells only when loaded with synthetic H3.3K27M peptide (FIG. 12B). As an additional method to confirm the H3.3K27M- and HLA-A*02:01-specific cytotoxicity of TCR-transduced T-cells, we employed Carboxyfluorescein succinimidyl ester (CFSE)-stained target cells (U87H3.3K27M and U87H3.3WT cells) in the co-culture assay and evaluated the expression of 7-aminoactinomycin D (7-AAD) on the CFSE$^+$ target cells as an early marker for cell death (24). Our results confirmed those obtained by LDH-based assay (FIG. 12C). These results indicate that TCR-transduced T-cells are able to recognize the H3.3K27M epitope that is processed and presented by H3.3K27M$^+$HLA-A*02:01$^+$ glioma cells and specifically lyse those glioma cells.

Figure 13A:
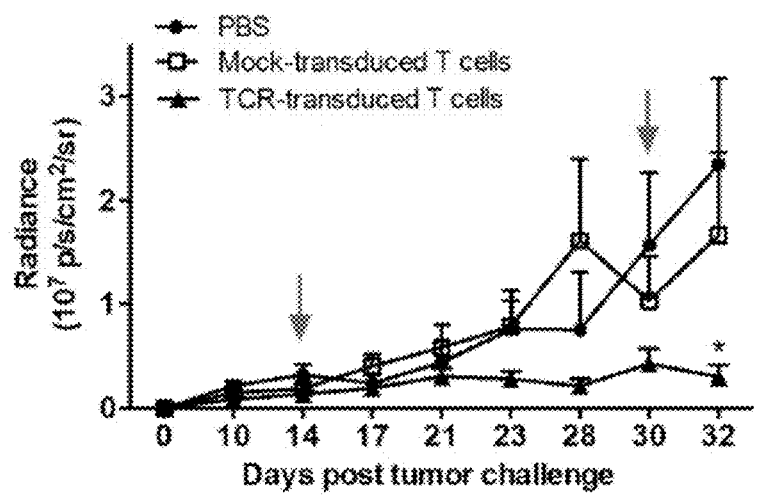
FIG. 13A-C. Adoptive transfer of TCR-transduced T-cells but not mock-transduced T-cells results in inhibition of intracranial H3.3K27M$^+$ glioma in NSG mice. NSG mice bearing intracranial U87H3.3K27M luciferase$^+$ gliomas received intravenous infusion with PBS, mock-transduced T-cells or TCR-transduced T-cells. 13A. Tumor growth is presented as radiance (10$^7$ p/s/cm$^2$/r) using BLI (n=8 per group). Arrows indicate days on which mice received treatment. 13B. Representative BLI images of mice on Day 10 and on Day 32 post tumor inoculation. The background BLI signals were defined based on the levels seen in non-tumor bearing mice. 13C. Preferential accumulation of TCR$^+$ T-cells in the tumor site. At the time of intravenous infusion, approximately 50% and 30% of the infused CD8$^+$ and CD4$^+$ T-cells, respectively, were TCR-Dextramer$^+$. On Day 2 following second intravenous infusion, the percentage of Dextramer$^+$ cells among CD8$^+$ T-cells and CD4$^+$ T-cells were evaluated in the peripheral blood and the brain of mice that received TCR-transduced T-cells. Data indicate % Dextramer$^+$ cells among total live CD8$^+$ or CD4$^+$ T-cells (n=5 per group). *p<0.05, **p<0.01 using Student t test.
Figure 13B:
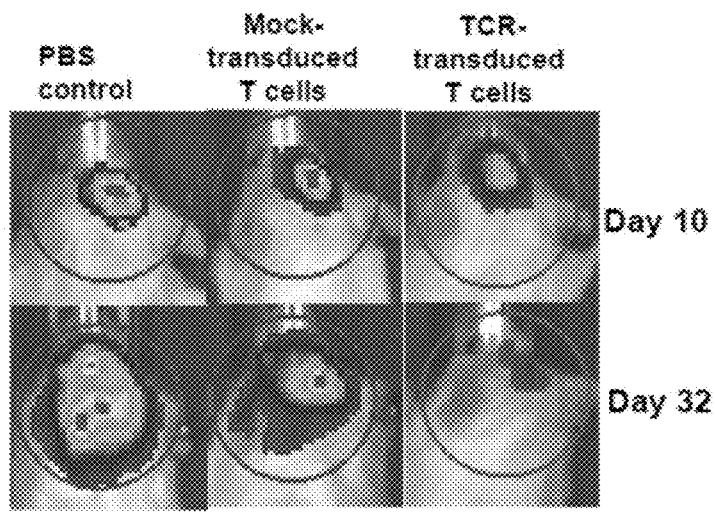
Figure 13C:
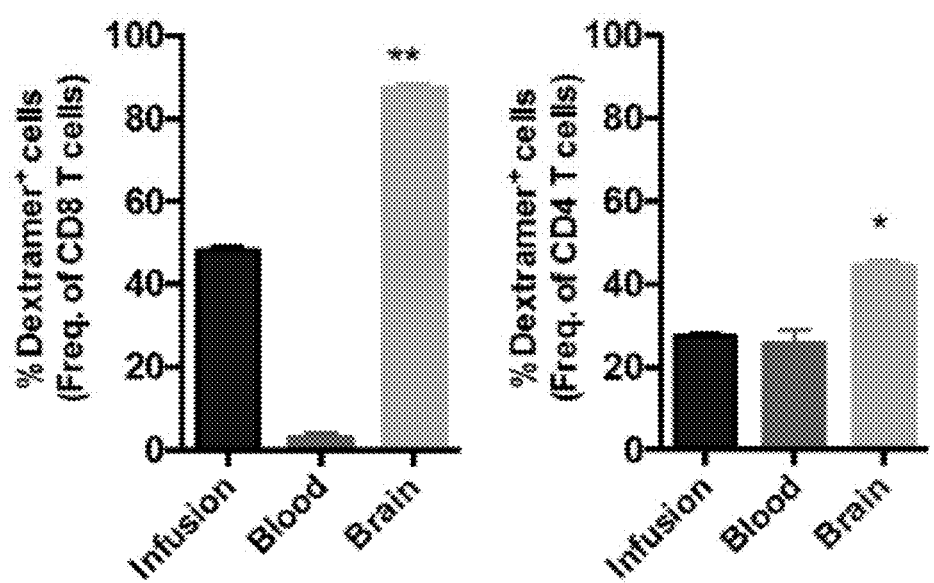

TCR-transduced T-cells Significantly Inhibit Progression of H3.3K27M$^+$ Glioma Xenograft To determine the preclinical therapeutic activities of TCR-transduced T-cells in vivo, we injected 5×10$^4$ U87H3.3K27M luciferase$^+$ cells into the brain of immunocompromised NSG mice on Day 0. On Day 14 and Day 30, mice with established tumors received intravenous injection of either PBS, 5×10$^6$ control mock-transduced T-cells, or 5×10$^6$ TCR-transduced T-cells. Bioluminescence imaging (BLI) indicated a significant reduction in the tumor burden in mice receiving TCR-transduced T-cells but not in mice receiving PBS or mock-transduced T-cells (FIGS. 13A and B). In an attempt to determine the accumulation of TCR-transduced T-cells in the intracranial xenograft, we euthanized the mice on Day 32 and evaluated tumor-infiltrating lymphocytes using the HLA-A*02:01-H3.3K27M$_{26-35}$ dextramer as well as anti-CD8 and anti-CD4 monoclonal antibodies. While the transduction efficiency of the infused CD8$^+$ and CD4$^+$ cells was approximately 50% and 30%, respectively (FIG. 13C), we found that over 80% and 40% of human CD8$^+$ and CD4$^+$ T-cells, respectively, were positive for the dextramer in the tumor. On the other hand, approximately 10% and 20% of CD8$^+$ and CD4$^+$ T-cells, respectively, were dextramer positive in the peripheral blood (FIG. 13C). These data suggest that there was a selective accumulation of TCR-transduced T-cells in the intracranial tumor site.

Materials and Methods

Cells and cell culture. DIPG neurosphere cultures were maintained in tumor stem media containing Neurobasal-A Medium (1×), DMEM/F-12, HEPES buffer, Sodium pyruvate, MEM non-essential amino acids, GlutaMAX-I, Anti-Anti solution, and B-27 supplement minus vitamin A or Gem21 neuroplex, all purchased from Life Technologies. Media was supplemented with 20 ng/mL recombinant human (rh) EGF (Peprotech; AF-100-15), 20 ng/mL rhFGF-basic (Peprotech; AF-100-18B), 10 ng/mL hPDGF-AA (Peprotech; 100-13A), 10 ng/mL hPDGF-BB (Peprotech; 100-14B) and 2 µg/ml Heparin solution (Sigma; H3149-10KU) at initiation of cell culture and weekly thereafter. Cells were passaged by trituration in TrypLE Express (Invitrogen; 12604-039) and DNase1 (Worthington; LS002007) followed by resuspension in fresh media. U87H3.3K27M and U87H3.3WT were generated by transfection of a PT2/C vector encoding cDNA for either WT H3.3 or the K27M H3.3 into parental U87MG cells using Fugene HD transfection reagent (Promega; E2311). Expression of H3.3K27M was confirmed by western blot analysis with an anti-H3.3K27M antibody (Millipore; ABE419). The Jurkat T-cell clone 76 (J76CD8) line (M. H. Heemskerk, M. Hoogeboom, R. A. de Paus, M. G. Kester, M. A. van der Hoorn, E. Goulmy, R. Willemze, J. H. Falkenburg, *Blood* 102, 3530-3540 (2003)), which are deficient in endogenous TCR α- and β-chains but express human CD8, was provided by Dr. Mirjam Heemskerk (Leiden University Medical Center, Leiden, Netherlands).

T-cell isolation. LRS chambers containing healthy donor-derived HLA-A*02:01$^+$ PBMCs were obtained from the Stanford Blood Bank (Stanford, Calif.). Patient-derived PBMCs were obtained through the IRB-approved Neurosurgery Tissue Bank (IRB/CHR#10-01318; PI Dr. Joanna Phillips) with coded tissue information without any protected health identifiers. T-cells were enriched from whole blood by immunodensity isolation using the RosetteSep™ Human T-cell Enrichment Cocktail (Stemcell Technologies; 15061) according to the manufacturer's suggested protocol. T-cells were cryopreserved in RPMI media containing 20% human AB serum and 10% DMSO and stored at −196° C.

Peptides. The synthetic peptides H3.3K27M$_{26-35}$ (RMSAPSTGGV (SEQ ID NO:2)), H3.3WT$_{26-35}$ (RKSAPSTGGV (SEQ ID NO:3)), CITmH3.3$_{26-35}$ (XMSAPSTGGV (SEQ ID NO:18)), H3.1K27M$_{26-35}$ (RMSAPATGGV (SEQ ID NO:6)), CEF1$_{58-66}$ Influenza Matrix Protein M1 (GILGFVFTL (SEQ ID NO:19)), as well as peptides used for the alanine scanning assay were synthesized by A&A labs (San Diego, Calif.) and were >95% pure as indicated by analytic high-performance liquid chromatography and mass spectrometric analysis. Peptides were dissolved in DMSO at a concentration of 10 mg/mL and stored at −80° C. until use.

HLA-peptide binding assays. Quantitative assays to measure the binding of peptides to purified HLA A*02:01 class I molecules are based on the inhibition of binding of a radiolabeled standard peptide (HBV core 18-27 analog, FLPSDYFPSV (SEQ ID NO:20)), and were performed as detailed elsewhere (J. Sidney, S. Southwood, C. Moore, C.

Oseroff, C. Pinilla, H. M. Grey, A. Sette, *Curr Protoc Immunol Chapter* 18, Unit 18 13 (2013)). HLA molecules were purified by affinity chromatography from the EBV transformed homozygous cell line JY, as described previously (J. Sidney, S. Southwood, C. Moore, C. Oseroff, C. Pinilla, H. M. Grey, A. Sette, *Curr Protoc Immunol Chapter* 18, Unit 18 13 (2013)). Peptides were tested at six different concentrations covering a 100,000-fold dose range in three or more independent assays, and the concentration of peptide yielding 50% inhibition of the binding of the radiolabeled probe peptide ($IC_{50}$) was calculated. Under the conditions used, where [radiolabeled probe]<[MHC] and $IC_{50} \geq$ [MHC], the measured $IC_{50}$ values are reasonable approximations of the true $K_d$ values (K. Gulukota, J. Sidney, A. Sette, C. DeLisi, *J Mol Biol* 267, 1258-1267 (1997); Y. Cheng, W. H. Prusoff, *Biochemical Pharmacology* 22, 3099-3108 (1973)).

ELISPOT assays. Patient-derived PBMCs were stimulated with 10 µg/ml H3.3K27M$_{26-35}$ peptide or H3.3WT$_{26-35}$ peptide, or without peptide. At 48 hours, rhIL-2 (50 U/ml), IL-7 (10 ng/ml) and IL-15 (10 ng/ml) were added to the culture for an additional 5 days. Fifty thousand peptide stimulated T-cells were co-cultured with $5 \times 10^3$ T2 cells pulsed with 10 µg/ml H3.3K27M$_{26-35}$ peptide, H3.3WT$_{26-35}$ peptide, or without peptide for 24 hrs on the anti-human IFN-γ-antibody-coated ELISPOT plates. To determine TCR avidity, $5 \times 10^4$ TCR-transduced CD8$^+$ T-cells were co-cultured with $5 \times 10^4$ T2 cells pulsed with different concentrations of the H3.3K27M peptide overnight on the anti-human IFN-γ antibody-coated ELISPOT plates. The rest of the protocol was carried out according to the manufacturer's protocol (Human IFN-γ ELISPOT kit, BD, 552138). The spots were quantified using the CTL S6 Universal-V Analyzer ELISpot Reader (ImmunoSpot®).

Purification and LC-MS/MS analysis of HLA-class I peptides. HLA-class I complexes were purified from $5 \times 10^8$ U87 parental cells or U87 cells transfected with either WT H3.3 or H3.3K27M, as previously described (17). Briefly, cells were lysed with 0.25% sodium deoxycholate (Sigma-Aldrich), 1% octyl-β-D glucopyranoside (Sigma-Aldrich), 0.2 mM iodoacetamide, 1 mM EDTA, and 1:200 Protease Inhibitors Cocktail (Sigma-Aldrich) in PBS at 4° C. for 1 hour. The lysate was cleared by a 30 minute centrifugation at 40,000×g at 4° C. HLA-class I complexes were immunoaffinity-purified from the cleared lysate with Protein-A Sepharose beads (Invitrogen) covalently bound to the pan-HLA-class I antibody W6/32 (purified from HB95 cells, ATCC) and eluted at room temperature with 0.1 N acetic acid. Eluted HLA-I complexes were then loaded on Sep-Pak tC18 cartridges (Waters) and HLA-class I peptides were separated from the complexes by eluting them with 30% acetonitrile (ACN) in 0.1% trifluoroacetic acid (TFA). Peptides were further purified using Silica C-18 column tips (Harvard Apparatus), eluted again with 30% ACN in 0.1% TFA and concentrated by vacuum centrifugation. For LC-MS/MS analysis, HLA-class I peptides were separated on an EASY-nLC 1000 system (Thermo Fisher Scientific) coupled on-line to a Q Exactive HF mass spectrometer (Thermo Fisher Scientific) with a nanoelectrospray ion source (Thermo Fisher Scientific). Peptides were loaded in buffer A (0.1% formic acid) into a 50 cm long, 75 µm inner diameter column in house packed with ReproSil-Pur C18-AQ 1.9 µm resin (Dr. Maisch HPLC GmbH) and eluted with a 90 minute linear gradient of 5-30% buffer B (80% ACN, 0.1% formic acid) at a 250 nl/min flow rate. The Q Executive HF operated in a data dependent mode with full MS scans at the range of 300-1,650 m/z, with resolution of 60,000 at 200 m/z and the target value of $3 \times 10^6$ ions. The ten most abundant ions with charge between 1 and 3 were combined to give an AGC target value of $1 \times 10^5$ and for a maximum injection time of 120 ms and fragmented by higher-energy collisional dissociation (HCD). MS/MS scans were acquired with a resolution of 15,000 at 200 m/z and dynamic exclusion was set to 20 s in order to avoid repeated peptide sequencing. Data were acquired and analyzed with the Xcalibur software (Thermo Scientific). For the targeted identification of the H3.3K27M peptide, a heavy (Arg10) version of the peptide was synthetized with the Fmoc solid phase method using the ResPepMicroScale instrument (Intavis AG Bioanalytical instruments), introducing a 10.0083 Da mass difference with one $^{13}C6$ $^{15}N4$ arginine (AnaSpec Inc.). The heavy peptide was added to each sample at a 1 pmol/µl concentration for a total of 3 pmoles per run.

For mass spectrometry data analysis, raw files were processed using MaxQuant version 1.5.7.12 as described previously (M. Bassani-Sternberg, S. Pletscher-Frankild, L. J. Jensen, M. Mann, *Mol Cell Proteomics* 14, 658-673 (2015)). Searches were performed against the Human UniProt database (July 2015) and a customized reference database containing the H3.3K27M sequence. Enzyme specificity was set as unspecific and possible sequences matches were restricted to 8-15 amino acids and a maximum mass of 1500 Da. N-terminal acetylation and methionine oxidation were set as variable modifications. A false discovery rate of 0.01 was required at the peptide level. To identify the heavy peptide, an Arg10 label was added to the search type specification.

Induction and isolation of H3.3K27M-specific CTL clones. To generate dendritic cells, the plastic adherent cells from PBMCs were cultured in AIM-V medium (Invitrogen) supplemented with 1,000 units/mL recombinant human granulocyte macrophage colony-stimulating factor and 500 units/mL recombinant human IL-4 (rhIL-4; Cell Sciences) at 37° C. in a humidified $CO_2$ (5%) incubator. Six days later, the immature dendritic cells were stimulated with recombinant human tumor necrosis factor-α, IL-6, and IL-1β (10 ng/mL each). Mature dendritic cells were then harvested on day 8, resuspended in AIM-V medium at $1 \times 10^6$ cells per mL with peptide (10 µg/mL), and incubated for 2 hours at 37° C. Populations of autologous CD8$^+$ T-cells were enriched from PBMCs using magnetic microbeads (Miltenyi Biotech). CD8$^+$ T-cells ($2 \times 10^6$ per well) were co-cultured with $2 \times 10^5$ per well peptide-pulsed dendritic cells in 2 mL/well of AIM-V medium supplemented with 5% human AB serum, 10 units/mL rhIL-2 (R&D Systems, Minneapolis, Minn.), and 10 units/mL rhIL-7 (Cell Sciences) in each well of 24-well tissue culture plates. On day 15, lymphocytes were re-stimulated with autologous dendritic cells pulsed with peptide in AIM-V medium supplemented with 5% human AB serum, rhIL-2, and rhIL-7 (10 units/mL each).

HLA-A*0201-peptide tetramer staining. Phycoerythrin (PE)-conjugated HLA-A*0201 RMSAPSTGGV (SEQ ID NO:2) tetramer (H3.3K27M-tetramer) was produced by the National Institute of Allergy and Infectious Disease tetramer facility within the Emory University Vaccine Center (Atlanta, Ga.) using the peptide synthesized by A&A labs (San Diego; CA). PE-conjugated HLA-A*0201/RMSAPSTGGV (SEQ ID NO:2) Dextramer was purchased from Immudex (Denmark). Cells were stained with tetramer (10 µg/mL) or Dextramer in PBS containing 1% bovine serum albumin (FACS Buffer) for 15 minutes at 4° C. (for tetramer) or room temperature (for dextramer), followed by surface staining for various T-cell markers at 4° C. Cells were then washed with FACS Buffer (PBS containing 1% FBS). For some experiments, T-cells were stained with tetramer, followed by anti-human CD8 APC (Biolegend, 344722) and anti-human CD69 FITC (eBioscience, 11-0699-42).

ELISA. Media was collected and centrifuged at 500 g for 10 minutes to remove debris. The human IFN-γ (BD OptEIA, 555142) and human IL-2 (Thermo Fischer Scientific, EH2IL2), ELISA was carried out according to the manufacturer's protocol. Plates were analyzed on a Biotek Synergy2 microplate reader (Biotek) at wavelengths of 450 nm and a background of 550 nm.

Cloning of TCR. 5'-Rapid Amplification of cDNA Ends-PCR (RACE-PCR) was performed by SMARTer® RACE 5'/3' Kit (Clontech Laboratories; 634838). Briefly, Single RACE PCR product (~900 bp) was excised from a 1.2% agarose gel, purified by Zymoclean™ Gel DNA Recovery Kit (Zymo; D4001) and TOPO® cloned into pCR™-Blunt II-TOPO® using the Zero Blunt® TOPO® PCR Cloning Kit (Life Technologies; K2800-20SC). The cloned product was then transformed into MAX Efficiency® DH5α™ Competent cells (Life Technologies; 182580120) and plated on ampicillin-containing LB agar plates (TEKNOVA; L1004). LB agar plates were placed at 37° C. overnight to allow colonies to form. Selected clones from the resulting constructs were subjected to PCR amplification and sequencing (QuintaraBio; San Francisco, Calif.) by using the M13 (−21) forward primer (5' TGTAAAACGACGGCCAGT-3' (SEQ ID NO:21)) and M13 reverse primer (5'-CAGGAAACA-GCTATGAC-3' (SEQ ID NO:22)) for sequencing. Sequences were analyzed using SnapGene Viewer (Snap Gene, Chicago, Ill.).

Generation of siTCR retroviral producer cell lines. The siTCR system has been previously described (S. Okamoto, Y. Amaishi, Y. Goto, H. Ikeda, H. Fujiwara, K. Kuzushima, M. Yasukawa, H. Shiku, J. Mineno, *Mol Ther Nucleic Acids* 1, e63 (2012).; S. Okamoto, J. Mineno, H. Ikeda, H. Fujiwara, M. Yasukawa, H. Shiku, I. Kato, *Cancer Res* 69, 9003-9011 (2009)). Briefly, codon optimized TCRA and TCRB fragments were artificially synthesized and cloned into Takara's siTCR retroviral vector plasmid. PG13 packaging cells were plated at $3\times10^4$ cells per well of a six-well plate and incubated for 24 hours. PG13 cells were transfected with siTCR retroviral vector in the presence of 8 µg/mL of polybrene, and incubated for 4 hours at 37° C., 5% $CO_2$, this was repeated on the following day. The cells were further expanded and were then harvested as GaLV envelope pseudo-typed siTCR retroviral vector producer cells and were cryopreserved. For generation of retroviral particles, culture supernatant was collected from cells grown in complete DMEM media supplemented with 5 mM sodium butyrate (Sigma-Aldrich, 156-54-7) for 24 hours.

Infection of primary T-cells with siTCR vector. Human PBMCs were activated on plates pre-coated with anti-human CD3 antibody (OKT3 clone, Miltenyi Biotec, 170-076-124) and RetroNectin® (RN, Takara Bio, T100A). Three days after the stimulation, viral supernatant was spun on the RetroNectin coated plates at 2,000 g for 2 hrs at 4° C. Activated PBMCs were then added to the virus-coated RetroNectin plates using spinfection methodology at 1,000 g for 10 mins at 4° C., and the cells were supplemented with 600 U/ml IL-2 (Peprotech, 200-02). This transduction protocol was repeated on the next day, and PBMCs were allowed to rest for an additional 4 days and then stained with HLA-A*02:01-H3.3K27M tetramer to determine the transduction efficiency. The T-cells were maintained in 100 U/ml rhIL-2-containing freshly made GT-T551 media (Takara Bio, WK551S).

LDH-based cytotoxicity assay. The CytoTox 96 non-radioactive cytotoxicity assay (Promega) was carried out according to the manufacturer's protocol. Target cells were plated in 96 well plates with various Effector to Target ratios in 200 µL media for 24 hours. Fifty µL of supernatant was then transferred to an enzymatic assay plate containing 50 µl of CytoTox 96 Reagent and incubated for 30 minutes at room temperature. Stop solution was then added to each well and plates were analyzed at 490 nm on a Synergy2 microplate reader (Biotek). Percent cytotoxicity was calculated as [(Experimental−Effector spontaneous−Target Spontaneous)/(Target Maximum−Target Spontaneous)]×100.

CSFE-based cytotoxicity assay. Target cells were stained with carboxyfluorescein succinimidyl ester (CF SE) using the Vybrant® CFDA SE Cell Tracer Kit (Thermo Fisher Scientific, V12883). CF SE-labelled target cells ($5\times10^4$/well) were incubated with CTLs at the E/T ratio of 5 for 8 hours. To block HLA-A2-mediated lysis, anti-HLA-A2 antibody (10 µg/ml, Biolegend, 343302) was added to one group per experiment. At the end of incubation, 7-AAD (Biolegend, 420403) was added into each well and incubated for 10 minutes on ice. The samples were analyzed by flow cytometry, and the killed target cells were identified as $CFSE^+$7-$AAD^+$ cells. The cytotoxicity was calculated as the percentage of $CFSE^+$ and 7-$AAD^+$ cells in total $CFSE^+$ cells.

Therapy of mice bearing intracranial glioma xenografts. Five- to 6-week-old NOD.Cg-Prkdc$^{scid}$ Il2rg$^{tm1wjl}$/SzJ (NSG mice) female mice (Jackson Laboratory, Bar Harbor, Me.) were used in the experiments. Animals were handled in the Animal Facility at the University of California, San Francisco per an Institutional Animal Care and Use Committee-approved protocol. The procedure has been previously described by us (M. Ohno, T. Ohkuri, A. Kosaka, K. Tanahashi, C. H. June, A. Natsume, H. Okada, *Journal for Immunotherapy of Cancer* 1, 21 (2013)). Briefly, using a stereotactic apparatus, mice received $5\times10^4$ U87H3.3K27M cells/mouse in 2 µl PBS at 2 mm lateral to the bregma and 3 mm below the surface of the skull. After tumors were established, each mouse received intravenous infusion of PBS, mock-transduced T-cells or $5\times10^6$ TCR-transduced via the tail vein on Days 10 and 30 post tumor inoculation.

Bioluminescence imaging. The growth of luciferase positive U87H3.3K27M tumors in the brain was non-invasively monitored by BLI using the in vivo imaging system IVIS 100 (PerkinElmer, Alameda, Calif.). Mice received intraperitoneal injection with 200 µl (15 mg/ml) of freshly thawed aqueous solution of D-Luciferin potassium salt (PerkinElmer), were anesthetized with isoflurane, and imaged for bioluminescence for 1 min exposure time. Optical images were analyzed by IVIS Living Image software package.

Statistical analyses. All statistical analyses were carried out on Graphpad Prism software. For in vitro studies, Student t-test or one-way ANOVA were used to compare two groups or more than two groups, respectively. Non-linear regression analysis was used to determine the $EC_{50}$. We considered differences significant when p<0.05.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A T-cell expressing one or more polypeptides comprising a T-cell receptor (TCR) or fragment thereof that binds to a peptide/major histocompatibility complex (MHC) complex, wherein the peptide in the peptide/MHC complex consists of 10-12 amino acids and comprises (R/A)MSAP(S/A)TGGV (SEQ ID NO:1).

2. The T-cell of claim 1, wherein the TCR or fragment thereof is heterologous to the T-cell.

3. The T-cell of claim 1, wherein expression of the TCR or fragment thereof is under the control of a heterologous promoter.

4. The T-cell of claim 1, wherein the peptide consists of RMSAPSTGGV (SEQ ID NO:2).

* * * * *